United States Patent
Higgins et al.

(10) Patent No.: US 8,062,534 B2
(45) Date of Patent: Nov. 22, 2011

(54) APPARATUS AND METHOD FOR SEPARATING AND CONCENTRATING FLUIDS CONTAINING MULTIPLE COMPONENTS

(75) Inventors: Joel C. Higgins, Claypool, IN (US);
Matthew Swift, Fort Wayne, IN (US);
Nathan Gordon, Plymouth, IN (US);
Barry F. Hecker, Pierceton, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 0 days.

(21) Appl. No.: 12/961,191

(22) Filed: Dec. 6, 2010

(65) Prior Publication Data
US 2011/0077596 A1    Mar. 31, 2011

Related U.S. Application Data

(60) Division of application No. 11/441,276, filed on May 25, 2006, now Pat. No. 7,845,499, which is a continuation-in-part of application No. 10/932,882, filed on Sep. 2, 2004, now Pat. No. 7,374,678, which is a continuation-in-part of application No. 10/445,381, filed on May 23, 2003, now Pat. No. 7,179,391.

(60) Provisional application No. 60/383,013, filed on May 24, 2002.

(51) Int. Cl.
*B04B 5/02* (2006.01)

(52) U.S. Cl. ........ 210/787; 210/800; 210/789; 210/788; 210/360.1; 210/380.1; 494/43; 494/50; 494/67; 604/6.15; 604/403

(58) Field of Classification Search ............... 210/787, 210/788, 789, 800, 360.1, 380.1; 604/6.15, 604/403; 494/45, 50, 67
See application file for complete search history.

(56) References Cited

U.S. PATENT DOCUMENTS

| | | |
|---|---|---|
| 280,820 A | 7/1883 | Hickson et al. |
| 593,333 A | 11/1897 | Park |
| 1,468,313 A | 9/1923 | Lux |
| 1,593,814 A | 7/1926 | Vogel |
| 2,722,257 A | 11/1955 | Lockhart |

(Continued)

FOREIGN PATENT DOCUMENTS

AU         696278         1/1999

(Continued)

OTHER PUBLICATIONS

"Cell Isolation Techniques, Methods and Materials, Working with Enzymes," (2004) (9 pages) Worthington Biochemical Corp.

(Continued)

*Primary Examiner* — Tony G Soohoo
*Assistant Examiner* — David C Mellon
(74) *Attorney, Agent, or Firm* — Harness, Dickey

(57) ABSTRACT

An apparatus that allows for separating and collecting a fraction of a sample. The apparatus, when used with a centrifuge, allows for the creation of at various fractions in the apparatus. A buoy system that may include a first buoy portion and a second buoy member operably interconnected may be used to form at least three fractions from a sample during a substantially single centrifugation process. Therefore, the separation of various fractions may be substantially quick and efficient. Also selected fractions from the sample can be applied to a patient, either alone or as part of a mixture.

22 Claims, 16 Drawing Sheets

U.S. PATENT DOCUMENTS

| | | |
|---|---|---|
| 3,013,557 A | 12/1961 | Pallotta |
| 3,159,159 A | 12/1964 | Cohen |
| 3,409,165 A | 11/1968 | Creith |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,545,671 A | 12/1970 | Ross |
| 3,596,652 A | 8/1971 | Winkelman |
| 3,706,305 A | 12/1972 | Berger et al. |
| 3,706,306 A | 12/1972 | Berger et al. |
| 3,723,244 A | 3/1973 | Breillatt, Jr. |
| 3,779,383 A | 12/1973 | Ayres |
| 3,785,549 A | 1/1974 | Latham, Jr. |
| 3,814,248 A | 6/1974 | Lawhead |
| 3,850,369 A | 11/1974 | Bull et al. |
| 3,879,295 A | 4/1975 | Glover et al. |
| 3,894,952 A | 7/1975 | Ayres |
| 3,896,733 A | 7/1975 | Rosenberg |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,937,211 A | 2/1976 | Merten |
| 3,941,699 A | 3/1976 | Ayres |
| 3,951,801 A | 4/1976 | Ayres |
| 3,957,654 A | 5/1976 | Ayres |
| 3,965,889 A | 6/1976 | Sachs |
| 3,972,812 A | 8/1976 | Gresl, Jr. |
| 3,982,691 A | 9/1976 | Schlutz |
| 4,001,122 A | 1/1977 | Griffin |
| 4,020,831 A | 5/1977 | Adler |
| 4,046,699 A | 9/1977 | Zine, Jr. |
| 4,055,501 A | 10/1977 | Cornell |
| 4,059,108 A | 11/1977 | Latham, Jr. |
| 4,077,396 A | 3/1978 | Wardlaw et al. |
| 4,088,582 A | 5/1978 | Murty et al. |
| 4,146,172 A | 3/1979 | Cullis et al. |
| 4,152,270 A | 5/1979 | Cornell |
| 4,154,690 A | 5/1979 | Ballies et al. |
| 4,159,896 A | 7/1979 | Levine et al. |
| 4,187,979 A | 2/1980 | Cullis et al. |
| 4,204,537 A | 5/1980 | Latham, Jr. |
| 4,225,580 A | 9/1980 | Rothman et al. |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,362,567 A | 12/1982 | Schwarz et al. |
| 4,364,832 A | 12/1982 | Ballies et al. |
| 4,377,572 A | 3/1983 | Schwarz et al. |
| 4,379,849 A | 4/1983 | Heimreid |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi et al. |
| 4,427,650 A | 1/1984 | Stroetmann et al. |
| 4,427,651 A | 1/1984 | Stroetmann et al. |
| 4,442,655 A | 4/1984 | Stroetmann et al. |
| 4,443,345 A | 4/1984 | Wells |
| 4,446,021 A | 5/1984 | Aufderhaar et al. |
| 4,453,927 A | 6/1984 | Sinko |
| 4,453,939 A | 6/1984 | Zimmerman et al. |
| 4,464,167 A | 8/1984 | Schoendorfer et al. |
| 4,511,662 A | 4/1985 | Baran et al. |
| 4,537,767 A | 8/1985 | Rothman et al. |
| RE32,089 E | 3/1986 | Blatt et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,735,616 A | 4/1988 | Eibl et al. |
| 4,735,726 A | 4/1988 | Duggins |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,844,818 A | 7/1989 | Smith |
| 4,846,835 A | 7/1989 | Grande |
| 4,850,952 A | 7/1989 | Figdor et al. |
| 4,853,137 A | 8/1989 | Ersson et al. |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,902,281 A | 2/1990 | Avoy |
| 4,909,251 A | 3/1990 | Seelich et al. |
| 4,917,801 A | 4/1990 | Luderer et al. |
| 4,928,603 A | 5/1990 | Rose et al. |
| 4,929,242 A | 5/1990 | Desecki et al. |
| 4,939,081 A | 7/1990 | Figdor et al. |
| 4,943,273 A | 7/1990 | Pages et al. |
| 4,946,601 A | 8/1990 | Fiehler |
| 4,957,637 A | 9/1990 | Cornell |
| 4,957,638 A | 9/1990 | Smith |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,024,613 A | 6/1991 | Vasconcellos et al. |
| 5,030,215 A | 7/1991 | Morse et al. |
| 5,030,341 A | 7/1991 | McEwen et al. |
| 5,045,048 A | 9/1991 | Kaleskas et al. |
| 5,047,004 A | 9/1991 | Wells |
| 5,053,127 A | 10/1991 | Schoendorfer et al. |
| 5,053,134 A | 10/1991 | Luderer et al. |
| 5,071,570 A | 12/1991 | Shiraki et al. |
| 5,080,262 A | 1/1992 | Herold et al. |
| 5,086,784 A | 2/1992 | Levine et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson et al. |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al. |
| 5,178,602 A | 1/1993 | Wells |
| 5,185,001 A | 2/1993 | Galanakis |
| 5,190,057 A | 3/1993 | Sarfarazi |
| 5,190,759 A | 3/1993 | Lindblad et al. |
| 5,197,985 A | 3/1993 | Caplan et al. |
| 5,203,825 A | 4/1993 | Haynes et al. |
| 5,204,537 A | 4/1993 | Bennet et al. |
| 5,206,023 A | 4/1993 | Hunziker et al. |
| 5,207,638 A | 5/1993 | Choksi et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,226,914 A | 7/1993 | Caplan et al. |
| 5,234,608 A | 8/1993 | Duff |
| 5,236,604 A | 8/1993 | Fiehler |

| | | | | | | |
|---|---|---|---|---|---|---|
| 5,251,786 A | 10/1993 | Sarrine | | 5,811,151 A | 9/1998 | Hendriks et al. |
| 5,258,126 A | 11/1993 | Pall et al. | | 5,817,519 A | 10/1998 | Zelmanovic et al. |
| 5,260,420 A | 11/1993 | Burnouf-Radosevich et al. | | 5,823,986 A | 10/1998 | Peterson |
| 5,269,927 A | 12/1993 | Fiehler | | 5,824,084 A | 10/1998 | Muschler |
| 5,271,852 A | 12/1993 | Luoma, II | | 5,830,359 A | 11/1998 | Knight et al. |
| 5,279,825 A | 1/1994 | Wehling et al. | | 5,833,866 A | 11/1998 | Brown |
| 5,281,342 A | 1/1994 | Biesel et al. | | 5,834,418 A | 11/1998 | Brazeau et al. |
| 5,290,552 A | 3/1994 | Sierra et al. | | 5,837,150 A | 11/1998 | Langley et al. |
| 5,290,918 A | 3/1994 | Bui-Khac et al. | | 5,840,502 A | 11/1998 | Van Vlasselaer |
| 5,298,171 A | 3/1994 | Biesel et al. | | 5,860,937 A | 1/1999 | Cohen |
| 5,304,372 A | 4/1994 | Michalski et al. | | 5,863,892 A | 1/1999 | Stern et al. |
| 5,316,674 A | 5/1994 | Pall et al. | | 5,865,785 A | 2/1999 | Bischof |
| 5,318,524 A | 6/1994 | Morse et al. | | 5,889,584 A | 3/1999 | Wardlaw |
| 5,318,782 A | 6/1994 | Weis-Fogh et al. | | 5,895,346 A | 4/1999 | Wells et al. |
| 5,321,126 A | 6/1994 | van Dommelen et al. | | 5,899,874 A | 5/1999 | Jonsson et al. |
| 5,322,620 A | 6/1994 | Brown et al. | | 5,900,245 A | 5/1999 | Sawhney et al. |
| 5,330,974 A | 7/1994 | Pines et al. | | 5,906,934 A | 5/1999 | Grande et al. |
| 5,344,752 A | 9/1994 | Murphy | | 5,916,557 A | 6/1999 | Berlowitz-Tarrant et al. |
| 5,370,802 A | 12/1994 | Brown | | 5,916,743 A | 6/1999 | Lake et al. |
| 5,376,263 A | 12/1994 | Fischel | | 5,918,622 A | 7/1999 | Perez et al. |
| 5,387,187 A | 2/1995 | Fell et al. | | 5,924,972 A | 7/1999 | Turvaville et al. |
| 5,393,674 A | 2/1995 | Levine et al. | | 5,934,803 A | 8/1999 | Hutter |
| 5,395,923 A | 3/1995 | Bui-Khac et al. | | 5,938,621 A | 8/1999 | Kelly et al. |
| 5,403,272 A | 4/1995 | Deniega et al. | | 5,955,032 A | 9/1999 | Kelly et al. |
| 5,405,607 A | 4/1995 | Epstein | | 5,955,436 A | 9/1999 | Kunkle, Jr. |
| 5,411,885 A | 5/1995 | Marx | | 5,958,250 A | 9/1999 | Brown et al. |
| 5,417,650 A | 5/1995 | Gordon | | 5,958,253 A | 9/1999 | Holm et al. |
| 5,420,250 A | 5/1995 | Lontz | | 5,980,734 A | 11/1999 | Itoh et al. |
| 5,443,481 A | 8/1995 | Lee | | 6,010,627 A | 1/2000 | Hood, III |
| 5,454,958 A | 10/1995 | Fiehler | | 6,022,306 A | 2/2000 | Dumont et al. |
| 5,456,693 A | 10/1995 | Conston et al. | | 6,025,201 A | 2/2000 | Zelmanovic et al. |
| 5,456,885 A | 10/1995 | Coleman et al. | | 6,027,655 A | 2/2000 | Holm |
| 5,474,687 A | 12/1995 | Van Vlasselaer | | 6,049,026 A | 4/2000 | Muschler |
| 5,486,359 A | 1/1996 | Caplan et al. | | 6,051,146 A | 4/2000 | Green et al. |
| 5,494,578 A | 2/1996 | Brown et al. | | 6,051,147 A | 4/2000 | Bischof |
| 5,494,592 A | 2/1996 | Latham, Jr. et al. | | 6,053,856 A | 4/2000 | Hlavinka |
| 5,501,371 A | 3/1996 | Schwartz-Feldman | | 6,054,122 A | 4/2000 | MacPhee et al. |
| 5,505,685 A | 4/1996 | Antwiler | | 6,063,297 A | 5/2000 | Antanavich et al. |
| 5,510,102 A | 4/1996 | Cochrum | | 6,063,624 A | 5/2000 | Kandler et al. |
| 5,533,518 A | 7/1996 | Vogler | | 6,071,421 A | 6/2000 | Brown |
| 5,560,830 A | 10/1996 | Coleman et al. | | 6,071,422 A | 6/2000 | Hlavinka et al. |
| 5,575,778 A | 11/1996 | Hardt et al. | | 6,071,423 A | 6/2000 | Brown et al. |
| 5,577,513 A | 11/1996 | Van Vlasselaer | | 6,090,793 A | 7/2000 | Zimmermann et al. |
| 5,585,007 A | 12/1996 | Antanavich et al. | | 6,096,309 A | 8/2000 | Prior et al. |
| 5,588,958 A | 12/1996 | Cunningham et al. | | 6,117,425 A | 9/2000 | MacPhee et al. |
| 5,589,462 A | 12/1996 | Patat et al. | | 6,123,655 A * | 9/2000 | Fell .................. 494/50 |
| 5,601,727 A | 2/1997 | Bormann et al. | | 6,150,163 A | 11/2000 | McPherson et al. |
| 5,607,579 A | 3/1997 | Latham, Jr. et al. | | 6,153,113 A | 11/2000 | Goodrich et al. |
| 5,614,106 A | 3/1997 | Payrat et al. | | 6,183,737 B1 | 2/2001 | Zaleske et al. |
| 5,618,663 A | 4/1997 | Delmas et al. | | 6,196,987 B1 | 3/2001 | Holmes et al. |
| 5,632,895 A | 5/1997 | Tsukagoshi et al. | | 6,197,325 B1 | 3/2001 | MacPhee et al. |
| 5,632,905 A | 5/1997 | Haynes | | 6,200,287 B1 | 3/2001 | Keller et al. |
| 5,641,414 A | 6/1997 | Brown | | 6,200,606 B1 | 3/2001 | Peterson et al. |
| 5,641,622 A | 6/1997 | Lake et al. | | 6,214,338 B1 | 4/2001 | Antanavich et al. |
| 5,643,192 A | 7/1997 | Hirsh et al. | | 6,221,315 B1 | 4/2001 | Giesler et al. |
| 5,645,540 A | 7/1997 | Henniges et al. | | 6,245,900 B1 | 6/2001 | Yamasaki et al. |
| 5,646,004 A | 7/1997 | Van Vlasselaer | | 6,264,890 B1 | 7/2001 | Boehringer et al. |
| 5,648,223 A | 7/1997 | Van Vlasselaer | | 6,274,090 B1 | 8/2001 | Coelho et al. |
| 5,649,903 A | 7/1997 | Deniega et al. | | 6,277,961 B1 | 8/2001 | Hock et al. |
| 5,663,051 A | 9/1997 | Vlasselaer | | 6,280,400 B1 | 8/2001 | Niermann |
| 5,674,173 A | 10/1997 | Hlavinka et al. | | 6,296,602 B1 | 10/2001 | Headley |
| 5,707,331 A | 1/1998 | Wells et al. | | 6,316,247 B1 | 11/2001 | Katz et al. |
| 5,707,647 A | 1/1998 | Dunn et al. | | 6,322,785 B1 | 11/2001 | Landesberg et al. |
| 5,707,876 A | 1/1998 | Levine | | 6,327,491 B1 | 12/2001 | Franklin et al. |
| 5,716,616 A | 2/1998 | Prockop et al. | | 6,328,765 B1 | 12/2001 | Hardwick et al. |
| 5,723,331 A | 3/1998 | Tubo et al. | | 6,342,157 B1 | 1/2002 | Hood, III |
| 5,724,988 A | 3/1998 | Dennehey et al. | | 6,351,659 B1 | 2/2002 | Vilsmeier |
| 5,733,466 A | 3/1998 | Benebo et al. | | 6,355,239 B1 | 3/2002 | Bruder et al. |
| 5,733,545 A | 3/1998 | Hood, III | | 6,368,298 B1 | 4/2002 | Beretta et al. |
| 5,736,033 A | 4/1998 | Coleman et al. | | 6,368,498 B1 | 4/2002 | Guilmette |
| 5,738,796 A | 4/1998 | Bormann et al. | | 6,398,972 B1 | 6/2002 | Blasetti et al. |
| 5,750,025 A | 5/1998 | Holmes et al. | | 6,406,671 B1 | 6/2002 | DiCesare et al. |
| 5,785,700 A | 7/1998 | Olson | | 6,410,344 B1 | 6/2002 | Chung et al. |
| 5,786,217 A | 7/1998 | Tubo et al. | | 6,417,004 B1 | 7/2002 | Brady et al. |
| 5,788,662 A | 8/1998 | Antanavich et al. | | 6,440,444 B2 | 8/2002 | Boyce et al. |
| 5,795,489 A | 8/1998 | Holm et al. | | 6,444,228 B1 | 9/2002 | Baugh et al. |
| 5,795,571 A | 8/1998 | Cederholm-Williams et al. | | 6,472,162 B1 | 10/2002 | Coelho et al. |
| 5,795,751 A | 8/1998 | Apel | | 6,508,778 B1 | 1/2003 | Verkaart et al. |
| 5,811,094 A | 9/1998 | Caplan et al. | | 6,516,953 B1 | 2/2003 | DiCesare et al. |

| | | |
|---|---|---|
| 6,523,698 B1 | 2/2003 | Dennehey et al. |
| 6,544,162 B1 | 4/2003 | Van Wie et al. |
| 6,558,341 B1 | 5/2003 | Swisher |
| 6,596,180 B2 | 7/2003 | Baugh et al. |
| 6,629,919 B2 | 10/2003 | Egozy et al. |
| 6,676,629 B2 | 1/2004 | Andrew et al. |
| 6,719,901 B2 | 4/2004 | Dolecek et al. |
| 6,733,471 B1 | 5/2004 | Ericson et al. |
| 6,758,978 B1 | 7/2004 | Bedell |
| 6,777,231 B1 | 8/2004 | Katz et al. |
| 6,803,022 B2 | 10/2004 | DiCesare et al. |
| 6,811,777 B2 | 11/2004 | Mishra |
| 6,835,377 B2 | 12/2004 | Goldberg et al. |
| RE38,730 E | 4/2005 | Wells et al. |
| 6,899,813 B2 | 5/2005 | Dolecek et al. |
| 6,905,612 B2 | 6/2005 | Dorian et al. |
| 6,911,202 B2 | 6/2005 | Amir et al. |
| RE38,757 E | 7/2005 | Wells et al. |
| 7,011,644 B1 | 3/2006 | Andrew et al. |
| 7,077,273 B2 | 7/2006 | Ellsworth et al. |
| 7,077,827 B2 | 7/2006 | Greenfield |
| 7,179,391 B2 | 2/2007 | Leach et al. |
| 7,195,606 B2 | 3/2007 | Ballin |
| 7,223,346 B2 | 5/2007 | Dorian et al. |
| 7,354,515 B2 | 4/2008 | Coull et al. |
| 7,374,678 B2 | 5/2008 | Leach et al. |
| 7,470,371 B2 * | 12/2008 | Dorian et al. ........... 210/787 |
| 7,553,413 B2 | 6/2009 | Dorian et al. |
| 2001/0009757 A1 | 7/2001 | Bischof et al. |
| 2002/0035820 A1 | 3/2002 | Farris |
| 2002/0076400 A1 | 6/2002 | Katz et al. |
| 2002/0082220 A1 | 6/2002 | Hoemann et al. |
| 2002/0090711 A1 | 7/2002 | Karlsson |
| 2002/0104808 A1 | 8/2002 | Blasetti et al. |
| 2002/0114775 A1 | 8/2002 | Pathak |
| 2002/0161449 A1 | 10/2002 | Muschler |
| 2002/0169408 A1 | 11/2002 | Beretta et al. |
| 2002/0172666 A1 | 11/2002 | Sacchi et al. |
| 2002/0182664 A1 | 12/2002 | Dolecek et al. |
| 2003/0033021 A1 | 2/2003 | Plouhar et al. |
| 2003/0033022 A1 | 2/2003 | Plouhar et al. |
| 2003/0050709 A1 | 3/2003 | Noth et al. |
| 2003/0050710 A1 | 3/2003 | Petersen et al. |
| 2003/0082152 A1 | 5/2003 | Hedrick et al. |
| 2003/0185803 A1 | 10/2003 | Kadiyala et al. |
| 2003/0191429 A1 | 10/2003 | Andrew et al. |
| 2003/0205538 A1 | 11/2003 | Dorian et al. |
| 2004/0120942 A1 | 6/2004 | McGinnis et al. |
| 2004/0171146 A1 | 9/2004 | Katz et al. |
| 2004/0182395 A1 | 9/2004 | Brookman |
| 2004/0182788 A1 | 9/2004 | Dorian et al. |
| 2004/0182795 A1 | 9/2004 | Dorian et al. |
| 2005/0076396 A1 | 4/2005 | Katz et al. |
| 2005/0084961 A1 | 4/2005 | Hedrick et al. |
| 2005/0084962 A1 | 4/2005 | Simon |
| 2005/0109716 A1 | 5/2005 | Leach et al. |
| 2005/0130301 A1 | 6/2005 | McKay et al. |
| 2005/0153441 A1 | 7/2005 | Hedrick et al. |
| 2005/0153442 A1 | 7/2005 | Katz et al. |
| 2005/0186120 A1 | 8/2005 | Dorian et al. |
| 2005/0196874 A1 | 9/2005 | Dorian et al. |
| 2005/0260174 A1 | 11/2005 | Fraser et al. |
| 2005/0260175 A1 | 11/2005 | Hedrick et al. |
| 2005/0282275 A1 | 12/2005 | Katz et al. |
| 2006/0051865 A1 | 3/2006 | Higgins et al. |
| 2006/0057693 A1 | 3/2006 | Simon |
| 2006/0083720 A1 | 4/2006 | Fraser et al. |
| 2006/0151384 A1 | 7/2006 | Ellsworth et al. |
| 2006/0175242 A1 | 8/2006 | Dorian et al. |
| 2006/0175244 A1 | 8/2006 | Dorian et al. |
| 2006/0196885 A1 | 9/2006 | Leach et al. |
| 2006/0243676 A1 | 11/2006 | Swift et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0034579 A1 | 2/2007 | Dorian et al. |
| 2007/0036768 A1 | 2/2007 | Fraser et al. |
| 2007/0075016 A1 | 4/2007 | Leach |
| 2007/0208321 A1 | 9/2007 | Leach et al. |
| 2008/0011684 A1 | 1/2008 | Dorian et al. |
| 2008/0164204 A1 | 7/2008 | Hatamian et al. |
| 2008/0173593 A1 | 7/2008 | Coull et al. |
| 2008/0193424 A1 | 8/2008 | McKale et al. |
| 2008/0210645 A1 | 9/2008 | Coull et al. |
| 2008/0217263 A1 | 9/2008 | Higgins et al. |
| 2008/0217264 A1 | 9/2008 | Leach et al. |
| 2008/0217265 A1 | 9/2008 | Leach et al. |
| 2008/0268064 A1 | 10/2008 | Woodell-May |
| 2008/0269762 A1 | 10/2008 | Simon et al. |
| 2008/0283474 A1 | 11/2008 | Leach et al. |
| 2008/0306431 A1 | 12/2008 | Yoo |
| 2009/0014391 A1 | 1/2009 | Leach et al. |
| 2009/0101599 A1 | 4/2009 | Dorian et al. |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2010/0055087 A1 | 3/2010 | Higgins et al. |
| 2010/0323870 A1 | 12/2010 | Leach et al. |
| 2010/0324450 A1 | 12/2010 | Leach et al. |

FOREIGN PATENT DOCUMENTS

| | | |
|---|---|---|
| BR | 9103724 | 3/1993 |
| CA | 1321138 | 8/1993 |
| CA | 2182862 | 6/1996 |
| CN | 1074709 | 7/1993 |
| DE | 56103 | 10/1860 |
| DE | 1443359 | 11/1968 |
| DE | 4202667 | 5/1993 |
| EP | 090997 | 10/1983 |
| EP | 0102773 | 3/1984 |
| EP | 0109374 | 5/1984 |
| EP | 0142339 | 5/1985 |
| EP | 0244834 A2 | 11/1987 |
| EP | 0253198 | 1/1988 |
| EP | 0295771 | 12/1988 |
| EP | 0417818 | 3/1991 |
| EP | 534178 | 3/1993 |
| EP | 0534178 | 3/1993 |
| EP | 0592242 | 4/1994 |
| EP | 1005910 | 6/2000 |
| EP | 1006360 | 6/2000 |
| EP | 1289618 | 3/2003 |
| EP | 1427279 A1 | 6/2004 |
| EP | 1467746 A2 | 10/2004 |
| EP | 1509326 | 3/2005 |
| EP | 1670315 A2 | 6/2006 |
| EP | 1716901 | 11/2006 |
| GB | 854715 | 11/1960 |
| JP | 60-053845 | 3/1985 |
| JP | 60250014 A | 12/1985 |
| JP | 2036872 | 2/1990 |
| JP | 02071747 | 3/1990 |
| JP | 02129224 | 10/2000 |
| WO | WO-8400905 | 3/1984 |
| WO | WO-8802259 | 4/1988 |
| WO | WO-9010031 | 9/1990 |
| WO | WO-9222312 | 12/1992 |
| WO | WO-9305067 | 3/1993 |
| WO | WO-9308904 | 5/1993 |
| WO | WO-9407548 | 4/1994 |
| WO | WO-9617871 | 6/1996 |
| WO | WO-9617871 A1 | 6/1996 |
| WO | WO-0061256 | 10/2000 |
| WO | WO-0103756 | 1/2001 |
| WO | WO-0183068 | 11/2001 |
| WO | WO-0238610 A1 | 5/2002 |
| WO | WO-02060925 A1 | 8/2002 |
| WO | WO-03015800 | 2/2003 |
| WO | WO-03024215 A1 | 3/2003 |
| WO | WO-03053362 A2 | 7/2003 |
| WO | WO-03088905 | 10/2003 |
| WO | WO-03092894 | 11/2003 |
| WO | WO-03099412 A1 | 12/2003 |
| WO | WO-2004009207 | 1/2004 |

| | | |
|---|---|---|
| WO | WO-2004104553 | 12/2004 |
| WO | WO-2005034843 A2 | 4/2005 |
| WO | WO-2007142908 A1 | 12/2007 |

OTHER PUBLICATIONS

"Cell Isolation Theory, Tissue Types," (2004) (5 pages) Worthington Biochemical Corp.

"Cytori Celution Cell Concentrate Device," Exhibit 14, 510(k) Summary, FDA approval K060482 (Sep. 28, 2006).

"Frequently Asked Questions, 1. Kits, 2. Engzymes," (2003) 3 pages Worthington Biochemical Corp.

"Trypsinization of Adherent Cells," (undated) 2 pages.

"Trypsinizing cells." Bart's Cookbook, Web. Apr. 14, 2010. http://pingu.salk.edu/~sefton/Hyper_protocols/trypsin.html.

Anesthesiology, vol. 81, No. 4, pp. 1074-1077, Oct. 1994, Hiromasa Mitsuhata, M.D., et al., "An Anaphylactic Reaction to Topical Fibrin Glue".

Ann Thorac Surg, vol. 53, pp. 530-531, 1992, Mehmet C. Oz, M.D., et al., "Autologous Fibrin Glue From Intraoperatively Collected Platelet-Rich Plasma".

Ann Thorac Surg, vol. 56, pp. 387-389, 1993, Robert L. Quigley, M.D., et al., "Intraoperative Procurement of Autologous Fibrin Glue".

Badiavas, et al., "Treatment of Chronic Wounds With Bone Marrow-Derived Cells," (Reprinted) Arch Dermatol. 139:510-516 (Apr. 2003).

Bang, N.U., et al., "Plasma Protein Requirements for Human Platelet Aggregation" Ann. N.Y. Acad Sci, 201:280-299 (1972).

Berguer, R., R. L. Staerkel, E. E. Moore, F. A. Moore, W. B. Galloway, and M. B. Mockus. "Warning: fatal reaction to the use of fibrin glue in deep hepatic wounds. Case reports." *J Trauma* 31 (3 1991): 408-11.

Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors," *J Thorac Cardiovasc Surg* 105 (5 1993): 892-7.

BioCUE™ Platelet Concentration System, Dec. 2010. (2 pages).

Biopolymers, vol. 27, pp. 763-774, 1988, Gerald Marx, "Mechanism of Fibrin Coagulation Based on Selective, Cation-Driven, Protofibral Association".

Brodke, et al., "Bone Grafts Prepared with Selective Cell Retention Technology Heal Canine Segmental Defects as Effectively as Autograft", SCR-Enriched Bone Crafts Heal Canine Segmental Defects, Journal of Orthopaedic Research (May 2006) pp. 857-866.

Casali, B., F. Rodeghiero, A. Tosetto, B. Palmieri, R. Immovilli, C. Ghedini, and P. Rivasi. "Fibrin glue from single-donation autologous plasmapheresis." Transfusion 32 (7 1992): 641-3.

CLOTALYST™ Automatic Clotting Factor, Would you like to have an autologous thrombin for rapid clotting and haemostasis?, brochure, Biomet Biologics, Inc., Feb. 2007 (12 pages).

Collier, B.S. et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda, Md. 20014, Blood, vol. 47, No. 5 (May 1976).

Connolly, "Injectable Bone Marrow Preparations to Stimulate Osteogenic Repair," Clinical Orthopaedics and Related Research 313:8-18 (1995).

Dallari, et al., "In Vivo Study on the Healing of Bone Defects Treated with Bone Marrow Stromal Cells, Platelet-Rich Plasma, and Freeze-Dried Bone Allografts, Alone and in Combination," Healing of Bone Defects, Journal of Orthopaedic Research (May 2006) pp. 877-888.

De Ugarte, et al., "Comparison of Multi-Lineage Cells from Human Adipose Tissue and Bone Marrow," Cells Tissues Organs 174:101-109 (2003).

De Ugarte, et al., "Differential Expression of Stem Cell Mobilization-Associated Molecules on Multi-Lineage Cells from Adipose Tissue and Bone Marrow," Immunology Letters 89:267-270 (2003).

DelRossi, A. J., A. C. Cernaianu, R. A.Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100 (2 1990): 281-6.

DeUgarte, M.D., Daniel A., et al., "Future of Fat as Raw Material for Tissue Regeneration," (2007) pp. 215-219, Lippincott Williams & Wilkins, Inc.

DiMuzio, Paul et al., "Development of a Tissue-Engineered Bypass Graft Seeded with Stem Cells," Vasucular, vol. 14, No. 6, (2006) pp. 338-342, BC Decker, Inc.

Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".

Edlich, Richard F., George T. Rodeheaver, and John G. Thacker. "Surgical Devices in Wound Healing Management." In *Wound Healing: Biochemical & Clinical Aspects*,ed. I. Kelman Cohen, Robert F. Diegelmann, and William J. Lindblad. 581-600. 1st ed., vol. Philadelphia: W.B. Saunders Company, 1992).

Eppley, et al., "Platelet Quantification and Growth Factor Analysis from Platelet-Rich Plasma: Implications for Wound Healing," Plastic and Reconstructive Surgery, 114(6):1502-1508 (Nov. 2004).

Epstein, G. H., R. A. Weisman, S. Zwillenberg, and A. D. Schreiber. "A new autologous fibrinogen-based adhesive for otologic surgery." *Ann Otol Rhinol Laryngol* 95 (1 Pt 1 1986): 40-5.

Fibrostik™ Plasma Concentrator, Attention Operating Surgeon, Cell Factor Technologies, Inc., Jul. 2003.

First clinical results: Kuderma, H. and Helene Matras. "Die klinische Anwendung der Klebung van Nervenanastomosen mit Gerinnungssubstanzen bei der Rekonstruction verletzter peripherer Nerven." Wein Klin Wochenschr 87 (15 1975): 495-501.

Floryan, K. et al. "Home Study Program: Intraoperative Use of Autologous Platelet-Rich and Platelet-Poor Plasma for Orthopedic Surgery Patients" vol. 80, No. 4 (Oct. 2004) p. 667-674.

Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.

Galois, et al., "Cartilage Tissue Engineering: State-of-the-Art and Future Approaches," Pathol Biol (Paris), 53(10), Dec. 2005.

Gibble, J. W. and P. M. Ness. "Fibrin glue: the perfect operative sealant?" *Transfusion* 30 (8 1990):741-7.

Gimble, Jeffrey M., "Adipose-Derived Stem Cells for Regenerative Medicine," Circulation Research (2007) pp. 1249-1260, American Heart Association, Inc.

Gomillion, Cheryl T., et al., "Stem cells and adipose tissue engineering," Biomaterials 27, Science Direct (2006) pp. 6052-6063, Elsevier.

GPS® III System, GPS® III Platelet Separation System, Leadership through Technology, brochure, Jul. 2007 (8 sheets).

GPS® System, "GPS® Platelet Concentrate System," Cell Factor Technologies, Inc., Biomet Orthopaedics, Inc., (2004) (9 pages).

GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.

GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.

GPS®II System, Gravitational Platelet Separation System, "Accelerating the Body's Natural Healing Process," Cell Factor Technologies, Inc., Biomet Europe (2005) 16 pages, http://www.cellfactortech.com/global_products.cfm, printed Sep. 16, 2005.

GPS®II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.

Grove, et al., "Plasticity of Bone Marrow-Derived Stem Cells," Stem Cells: Concise Review, Jan. 22, 2004.

Guilak, Frank, et al., "Adipose-derived adult stem cells for cartilage tissue engineering," Biorheology 41 (2004) pp. 389-399, IOS Press.

Harris, E.L.V. Concentration of the Extract. In. Protein Purification Methods: A Practical Approach Harris, E.L.V.; Angal, S.; Editors. (1989) Publisher: (IRL Press, Oxford, UK), pp. 67-69.

Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (3 1992): 357-9.
Harvest SmartPrep PRP-20 Procedure Pack, "Instructions for Use". Harvest Technologies brochure, SmartPrep2 (2002).
Hattori, et al., "Osteogenic Potential of Human Adipose Tissue-Derived Stromal Cells as an Alternative Stem Cell Source," Cells Tissues Organs (2004) 178:2-12 Karger.
Haynesworth, S.E. et al. "Mitogenic Stimulation of Human Mesenchymal Stem Cells by Platelet Releasate Suggests a Mechanism for Enhancement of Bone Repair by Platelet Concentrate" 48th Annual Meeting of the Orthopaedic Research Society Poster No. 0462 (2002).
Hennis, H. L., W. C. Stewart, and E. K. Jeter. "Infectious disease risks of fibrin glue [letter]." *Ophthalmic Surg* 23 (9 1992): 640.
Hernigou, et al., "Percutaneous Autologous Bone-Marrow Grafting for Nonunions. Influence of the Number and Concentration of Progenitor Cells," Journal of Bone & Joint Surgery, 87-A(7):1430-1437 (Jul. 2005).
International Preliminary Examination Report and Written Opinion issued Aug. 31, 2010 for PCT/US2009/035564 claiming benefit of U.S. Appl. No. 61/078,178, filed Jul. 3, 2008, which priority is also claimed of said provisional case by U.S. Appl. No. 12/395,085, filed Feb. 27, 2009.
International Preliminary Report on Patentability completed Aug. 13, 2009 for PCT/US2008/004687 claiming benefit of U.S. Appl. No. 60/911,407, filed Apr. 12, 2007.
International Search Report and Written Opinion mailed Jul. 2, 2008 for International Application No. PCT/US2008/004687 which claims priority to U.S. Appl. No. 60/911,407, filed Apr. 12, 2007.
International Search Report and Written Opinion mailed Jul. 3, 2009 for PCT/US2009/035564 claiming benefit of U.S. Appl. No. 61/078,178, filed Jul. 3, 2008.
International Search Report and Written Opinion mailed Jul. 30, 2010 for PCT/US2010/029957 which claims benefit of U.S. Appl. No. 12/417,789, filed Apr. 3, 2009.
International Search Report for International Application No. PCT/US/0316506 mailed Oct. 13, 2003 which claims benefit of U.S. Appl. No. 60/383,013, filed May 24, 2002.
International Search Report for International Application No. PCT/US2007/012587 mailed Nov. 6, 2007 which claims benefit of U.S. Appl. No. 11/441,276, filed May 25, 2006.
Ishida, et al., "Platelet-Rich Plasma With Biodegradable Gelatin Hydrogel Promotes Rabbit Meniscal Tissue Regeneration," 52nd Annual Meeting of the Orthopaedic Research Society Paper No. 1035, 1 page (2006).
Jackson, C. M. and Y. Nemerson. "Blood coagulation." *Annu Rev Biochem* 49 (811 1980): 765-811).
Jayadev, Suprya. "Trypsinization of Adherent Cells." Aug. 8, 1991. Web. Apr. 14, 2010 http://www.duke.edu/web/ceramide/protocols/0005.html.
Johnstone, et al., "Autologous Mesenchymal Progenitor Cells in Articular Cartilage Repair", Clinical Orthopaedics and Related Research 367S:S156-S162 (1999).
Jorgensen, et al., "Stem Cells for Repair of Cartilage and Bone: The Next Challenge in Osteoarthritis and Rheumatoid Arthritis," Annals of Rheumatic Diseases, Aug. 2000.
Journal of Oral Maxillofacial Surgery, vol. 43, pp. 605-611, 1985, Helene Matras, M.D., "Fibrin Seal: The State of the Art".
Karpatkin, S., "Heterogeneity of Human Platelets. VI., Correlation of Platelet Function with Platelet Volume", Blood, vol. 51, No. 2 (Feb. 1978).
Kjaergard, H. K,, U. S. Weis-Fogh, H. Sorensen, J. Thiis, and I. Rygg. "A simple method of preparation of autologous fibrin glue by means of ethanol." *Surg Gynecol Obstet* 175 (1 1992): 72-3.
Kjaergard, H. K., Fogh Us Weis, and J. J. Thiis. "Preparation of autologous fibrin glue from pericardial blood." *Ann Thorac Sur* 55 (2 1993): 543-4.
Laryngoscope vol. 99, pp. 974-976, Sep. 1989, Kyosti Laitakari, M.D., et al., "Autologous and Homologous Fibrinogen Sealants: Adhesive Strength".
Laryngoscope, vol. 95, pp. 1074-1076, Sep. 1985, Karl H. Siedentop, M.D., et al., "Autologous Fibrin Tissue Adhesive".
Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".
Lasher, Lisa, M.D., "My Experience with PRP," PowerPoint presentation, http://www.cellfactortech.com/global_products.cfm, printed Sep. 16, 2005.
Lendeckel, Stefan, et al., "Autologous stem cells (adipose) and fibrin glue used to treat widespread traumatic calvarial defects: case report," Journal of Cranio-Maxillofacial Surgery (2004) European Association for Cranio-Maxillofacial Surgery.
Lerner, R. and N. S. Binur. "Current status of surgical adhesives." *J Surg Res* 48 (2 1990): 165-81.
Lu, et al., "Bone Marrow Mesenchymal Stem Cells: Progress in Bone/Cartilage Defect Repair," 19(1), Jan. 2002.
Marrowstim Concentration System, Biomet Biologics, Inc., 20 pages (REV Feb. 15, 2008).
Matras, Helene, H. P. Dinges, H. Lassmann, and B. Mamoli. "Zur nahtlosen interfaszikulären Nerventransplantation im Tierexperiment." Wein Med Woschtr 122 (37 1972): 517-523.
Minntech® Filtration Technologies Group, "Hemocor HPH® Hemoconcentrator," Minntech Corporation (2004); http://www.minntech.com/ftg/products/hph/index.html, printed Jul. 15, 2004 (2 pages).
Minntech® Filtration Technologies Group, "Medical Applications: Blood Filtration" Minntech Corporation (2004); http://www.minntech.com/ftg/industries/medical/blood_filter.html, printed Jul. 15, 2004 (1 page).
Minntech® Filtration Technologies Group, "Renaflo® II Hemofilter," Minntech Corporation (2004); http://www.minntech.com/ftg/products/renaflo/index.html, printed Jul. 15, 2004 (2 pages).
Molnar, Amy, "Stem Cells from Muscles Can Repair Cartilage, Study Finds Genetically Engineered Muscle-Derived Stem Cells Improved Cartilage Repair in Rats", American College of Rheumatology, (2005).
Moretz, W., Jr., J Shea Jr., J. R. Emmett, and J Shea. "A simple autologous fibrinogen glue for otologic surgery." *Otolaryngol Head Neck Surg* 95 (1 1986): 122-4.
Nakagami, Hironori, et al., "Novel Autologous Cell Tehrapy in Ischemic Limb Disease Through Growth Factor Secretion by Cultured Adipose Tissue-Derived Stromal Cells," Angiogenesis by Adipose Tissue-Derived Cells, (2005) pp. 2542-2547, American Heart Association, Inc.
Nathan, Suresh,, et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.
Nilsson, et al., "Bone Repair Induced by Bone Morphogenetic Protein in Ulnar Defects in Dogs," The Journal of Bone and Joint Surgery, vol. 68 B., No. 4, Aug. 1986.
Otolaryngologic Clinics of North America, vol. 27, No. 1, pp. 203-209, Feb. 1994, Dean M. Toriumi, M.D., et al., "Surgical Tissue Adhesives in Otolaryngology-Head and Neck Surgery".
Parker, Anna M., et al., Adipose-derived stem cells for the regeneration of damaged tissues, Expert Opinion, Cell- & Tissue-based Therapy, Expert Opin. Biol. Ther. (2006) pp. 567-578 Informa UK Ltd.
Planat-Bénard, V., et al., "Spontaneous Cardiomyocyte Differentiation From Adipose Tissue Stroma Cells," Adipose-Derived Cell Cardiomyocyte (2004) pp. 223-229 American Heart Association, Inc.
Ponticiello, Michael S., "A Rapid Technique for the Isolation and Concentration of Stem Cells from Human Bone Marrow", Cell Factor Technologies, Inc. (2006) 2 pages.
Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.
Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Pub. 2005) pp. 1409-1422.
Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (2007) pp. 1423-1424.

Sanal, M. "Does fibrin glue cause foreign body reactions? [letter]." *Eur J Pediatr Surg* 3 (3 1993): 190 (1 page).

Sanal, M., H. Dogruyol, A. Gurpinar, and O. Yerci. "Does fibrin glue cause foreign body reactions?" *Eu r J Pediatr Surg* 2 (5 1992): 285-6.

Schmidt, K.G., et al., "Labelling of Human and Rabbit Platelets with Indium-Oxine Complex", 23:97-106 (1979).

Schmidt, K.G., et al., "Preparation of Platelet Suspensions from Whole Blood in Buffer", Scand. J. Hoemato, 23:88-96 (1979).

Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (2007) pp. 818-827 AlphaMed Press.

Sierra, D. H. "Fibrin sealant adhesive systems: a review of their chemistry, material properties and clinical applications." *J Biomater Appl* 7 (4 1993): 309-52.

Sigma-Aldrich® Alkaline Phosphatase (Procedure No. 85), drug fact sheet, (2003) pp. 1-2, Sigma-Aldrich, Inc.

Swift, Mathew J., et al., "Characterization of Growth Factors in Platelet Rich Plasma," 1-Cell Factor Technologies, http://www.cellfactortech.com/global_products.cfm, printed Sep. 16, 2005.

Symphony II Platelet Concentrate System/PCS brochure; "Increasing bone graft bioactivity through reproducible concentrations of natural growth factors," DePuy (Jan. 2003).

Takahashi, Kazutoshi et al., "Induction of Pluripotent Stem Cells from Adult Human Fibroblasts by Defined Factors," Cell, (2007) pp. 1-12, Elsevier Inc.

The American Journal of Surgery, vol. 168, pp. 120-122, Aug. 1994, Roy L. Tawes, Jr., M.D., et al., "Autologous Fibrin Glue: The Last Step in Operative Hemostatis".

The American Surgeon, vol. 55, pp. 166-168, Mar. 1989, William D. Spotnitz, M.D., et al., "Successful Use of Fibrin Glue During 2 Years of Surgery at a University Medical Center".

The Sports Medicine Center, "Knee Cartilage Implantation", Carticel™, "Autologous Cultured Chondrocyte Implantation", http://www.orthoassociates.com/carticel.htm (printed Apr. 6, 2006).

The Stone Clinic, "Platelet Rich Plasma (PRP)", web site printed May 2006.

Vox Sanquinis, vol. 68: 82-89, Feb. 1995, Boomgaard Et. al, Pooled Platelet Concentration Prepred by the . . .

Weis-Fogh, U. S. "Fibrinogen prepared from small blood samples for autologous use in a tissue adhesive system." *Eur Surg* Res 20 (5-6 1988): 381-9.

Wiseman, David M., David T. Rovee, and Oscar M. Alverez. "Wound Dressings: Design and Use." In *Wound Healing: Biochemical & Clinical Aspects*, ed. I. Kelman Cohen, Robert F. Diegelmann, and William J. Lindblad. 562-580. 1st ed., vol. Philadelphia: W. B. Saunders Company, 1992).

Woodell-May, et al., "Producing Accurate Platelet Counts for Platelet Rich Plasma: Validation of a Hematology Analyzer and Preparation Techniques for Counting," Scientific Foundation, Journal of Carniofacial Surgery 16(5):749-756 (Sep. 2005).

Written Opinion of the International Preliminary Examining Authority mailed Mar. 17, 2009 for International Application No. PCT/US2008/004687 which claims priority to U.S. Appl. No. 60/911,407, filed Apr. 12, 2007.

Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.

Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.

Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert, Inc.

Connolly, John, M.D., et al. "Development of an Osteogenic Bone-Marrow Preparation." The Journal of Bone and Joint Surgery, Incorporated. vol. 71-A, No. 5 (Jun. 1989) pp. 684-691.

\* cited by examiner

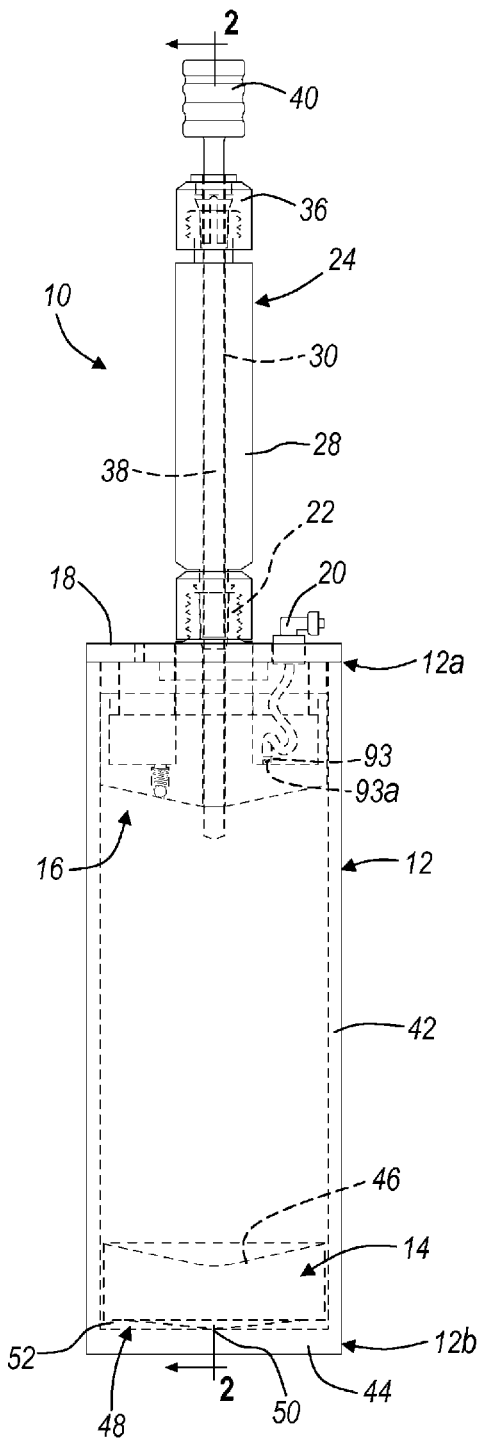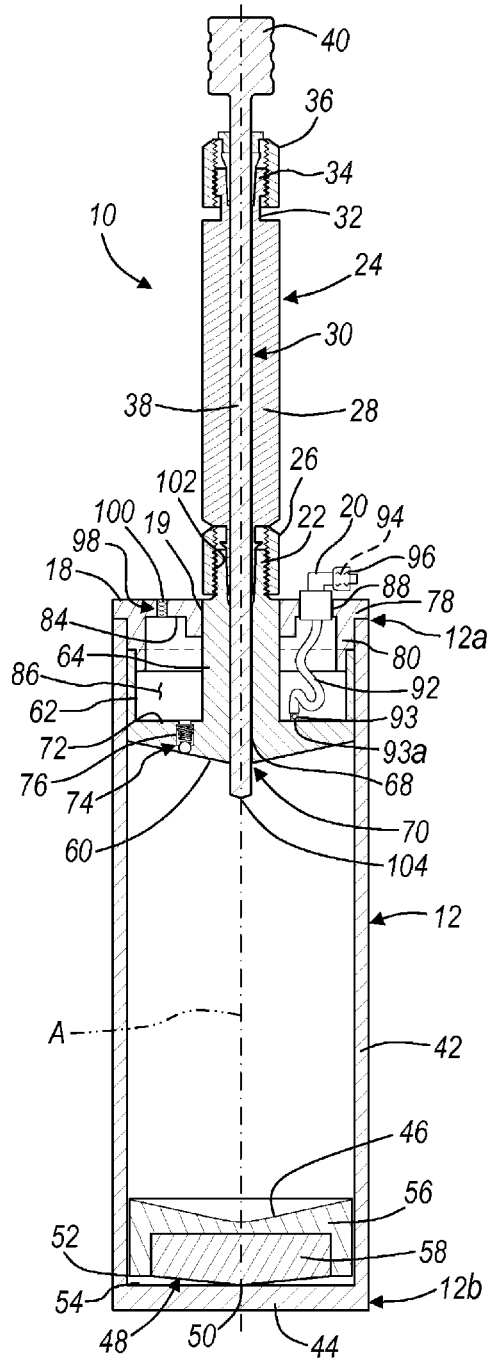
FIGURE 1
FIGURE 2

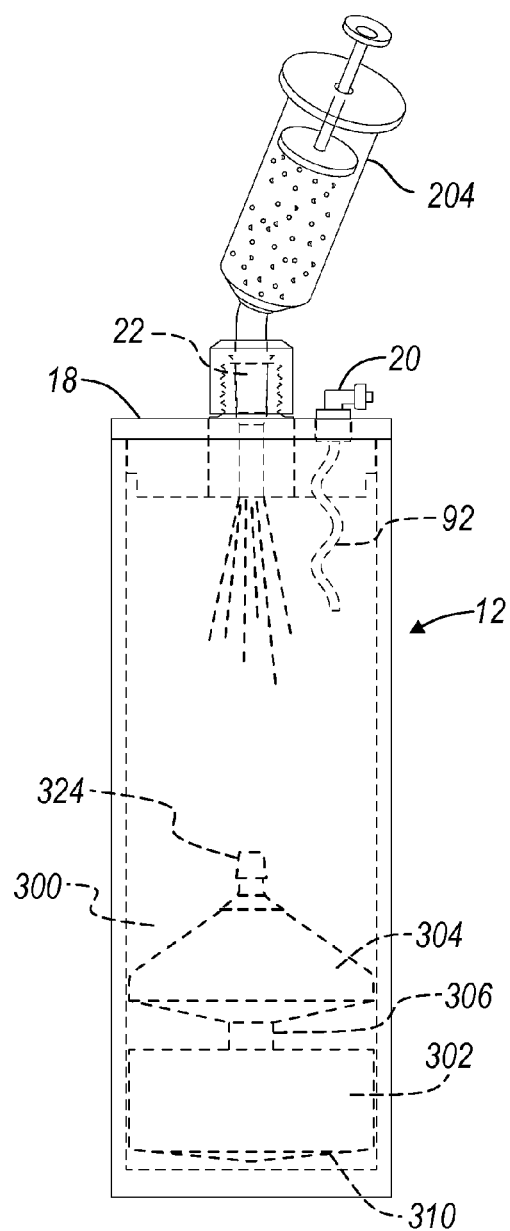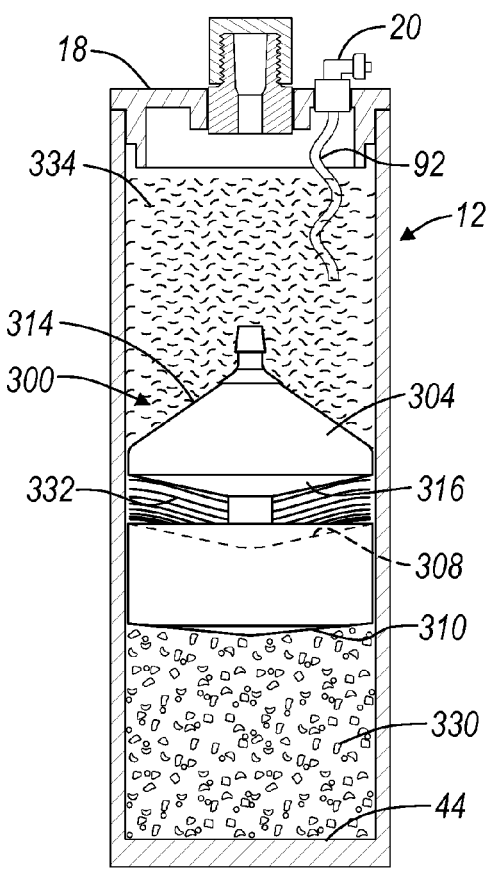
FIGURE 7A
FIGURE 7B

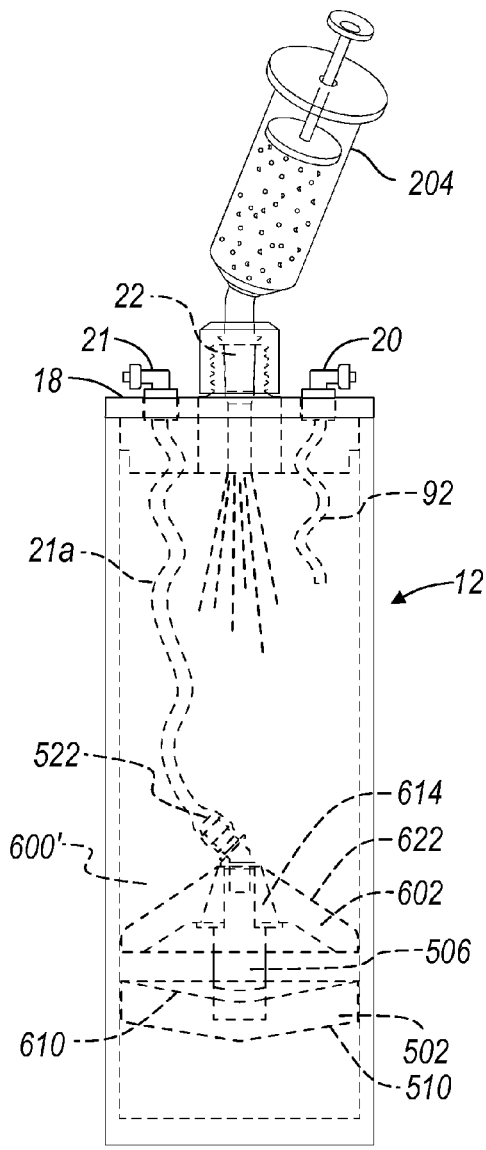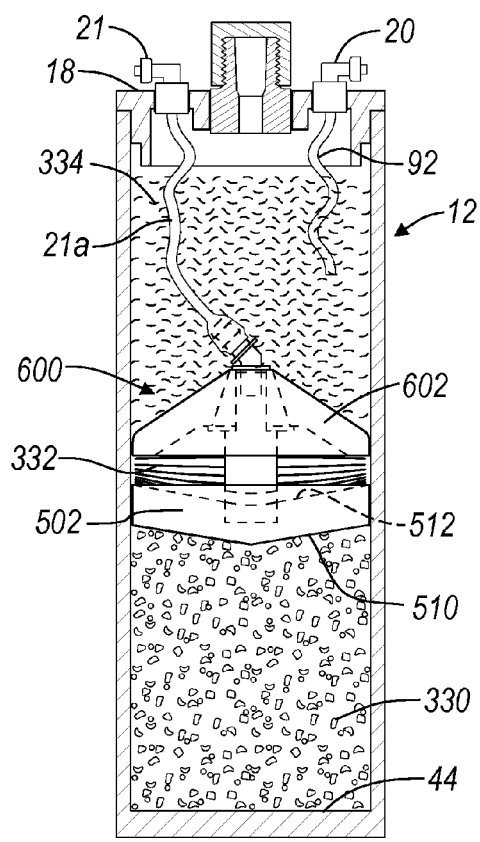
FIGURE 14A
FIGURE 14B

APPARATUS AND METHOD FOR SEPARATING AND CONCENTRATING FLUIDS CONTAINING MULTIPLE COMPONENTS

CROSS-REFERENCE TO RELATED APPLICATIONS

This application is a divisional of U.S. patent application Ser. No. 11/441,276 filed May 25, 2006, now U.S. Pat. No. 7,845,499, issued on Dec. 7, 2010 which is a continuation-in-part of U.S. patent application Ser. No. 10/932,882 filed Sep. 2, 2004, now U.S. Pat. No. 7,374,678, issued May 20, 2008, which is a continuation-in-part of U.S. patent application Ser. No. 10/445,381 filed May 23, 2003, now U.S. Pat. No. 7,179,391, issued Feb. 20, 2007, that claimed the benefit of U.S. Provisional Application No. 60/383,013, filed on May 24, 2002. The disclosures of the above applications are incorporated herein by reference.

FIELD

The present teachings relate to a multiple component fluid and a concentrator/separator, and more particularly relates to a container operable with a centrifuge to separate and concentrate various biological components.

BACKGROUND

Various fluids, such as whole blood or various other biological fluids may be separated into their constituent parts, also referred to as fractions or phases. For example, whole blood samples may include a plurality of constituents that may be separated by density in a device such as a centrifuge. The whole blood sample may be placed in a test tube, or other similar device, which is then spun in a centrifuge. In the centrifuge the whole blood is separated into different fractions depending upon the density of that fraction. The centrifugal force separates the blood or other sample into different fractions. In addition, various elements may be added to the test tube to create more than two fractions. In particular, commonly used gels may be used to divide the whole blood into a plurality of different fractions which may include fractions such as platelets, red blood cells, and plasma. Various other biological fluids may be separated as well. For example, nucleated cells may be separated and extracted from bone marrow or adipose tissue sample.

Many of these systems, however, do not provide a simple or efficient method to extract any more than one fraction and especially a fraction other than the top fraction. The top fraction of whole blood is plasma, or other blood constituents suspended in plasma. Thus, to extract other fractions the plasma fraction must either be removed and spun again to obtain the constituents suspended in this plasma. It is difficult to pierce the top fraction without co-mingling the sample. Accordingly, obtaining the other fractions is difficult with commonly known systems.

Other systems have attempted to alleviate this problem by providing a float or other device that is disposed within the sample at the interfaces of the different fractions during the centrifuge process. Nevertheless, these systems still do not allow a simple way to remove the different fractions without remixing the sample fractions. In addition, many of the systems do not allow an easy and reproducible method to remove the desired sample fraction.

Therefore, it is desired to provide a device to allow for the easy and reproducible removal of a particular fraction which does not happen to be the top fraction of a sample. It is desired to remove the required sample without mixing the different fractions during the extraction process. In addition, it is desired to provide a device which allows for a consistent extraction which includes known volumes or concentration of the fraction elements. Moreover, it is desired to separate and concentrate a selected fraction with one centrifugation step.

SUMMARY

An apparatus that separates and concentrates a selected fraction or component of a fluid, such as a biological fluid. For example, a buffy coat or platelet fraction or component of a whole blood sample or an undifferentiated cell component of bone marrow or adipose tissue sample. The apparatus, when used with a centrifuge, is generally able to create at least two fractions. It also provides for a new method of extracting the buffy coat fraction or component or middle fraction from a sample.

The apparatus includes a container to be placed in a centrifuge after being filled with a sample. A buoy or fraction separator, having a selected density that may be less than one fraction but greater than a second fraction, is disposed in the container. In addition, a second buoy may be placed in the container with the first. During the centrifuge processing, the buoy is forced away from a bottom of the container as the denser fraction collects at the bottom of the container. The buoy is generally able to physically separate the denser fraction from another fraction of the sample.

In addition to providing a first buoy and/or a second buoy, a buoy system may be provided. Generally, the buoy system may separate the sample into at least three fractions. The fractions may be separated or extracted from the container without substantially comingling the various fractions. Generally, a first buoy and a second buoy operate together to separate the sample into the various fractions and a syringe or tube may then be interconnected with a portion of the buoy system to extract the selected fractions. For example, a first buoy may be generally density tuned to a red blood cell fraction of a whole blood sample, and a second buoy tuned to a density less than the density of the plasma fraction.

According to various embodiments a method of forming an enriched scaffold for application relative to an anatomy is taught. The method may include obtaining a volume of a first whole material and obtaining a volume of a second whole material. A first fraction of the first whole material and a second fraction of the second whole material may be formed. At least one of the first fraction or the second fraction may be applied to the scaffold.

According to various embodiments a method of withdrawing a material directly from a patient and collecting a selected fraction of the material in a container is taught. The method may include forming an access to port to the patient. A pressure differential in a collection container may be formed relative to the patient. A connection may be made between the patient and the collection container via the port. The collection container may be filled with the material and separating the material to form the selected fraction.

Further areas of applicability of the present invention will become apparent from the detailed description provided hereinafter. It should be understood that the detailed description and specific examples, while indicating various embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a plan view of a separator including a depth gage affixed to a plunger in a tube according to a first embodiment of the present invention;

FIG. 2 is a cross-section view taken along line 2-2 of FIG. 1;

FIG. 6B is a cross-sectional view of the buoy system of FIG. 6a;

FIG. 7A is a plan view of a separator according to various embodiments being filled;

FIG. 7B is a plan view of a separator, according to various embodiments, after a centrifugation process;

FIG. 14A-14C is a plan view of a separator system in operation.

DETAILED DESCRIPTION OF VARIOUS EMBODIMENTS

The following description of various embodiments is merely exemplary in nature and is in no way intended to limit the invention, its application, or uses. Although the following description exemplary refers to a blood separation, it will be understood that the present invention may be used to separate and concentrate any appropriate material. It will be further understood that many multi-component or multi-fraction fluids may be separated. The components or fractions are generally inter-mingled in the whole sample but may be separated with a centrifuge device that causes increased local gravity or gravitational forces.

Figure 3:
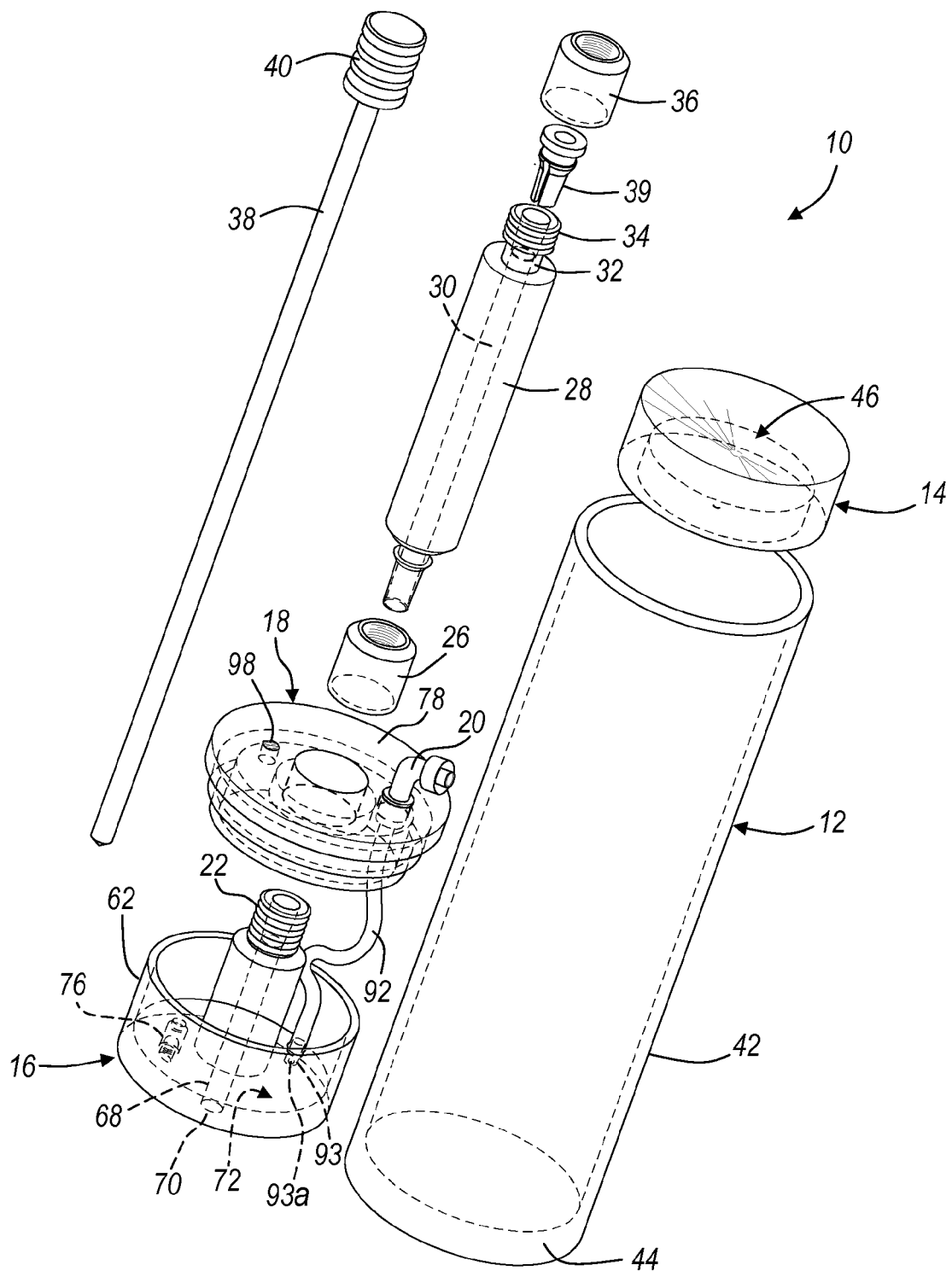
FIG. 3 is an exploded of the separator apparatus.

With reference to FIGS. 1-3, according to various embodiments a separator 10, also referred to as a concentrator, is illustrated according to a first embodiment of the present invention. The separator 10 generally includes a tube or container 12 that is adapted to hold a fluid sample, such as an anti-coagulated whole blood sample, for further processing. It will be understood that the tube may hold other solutions including constituents of more than one density, such as bone marrow or a mixture of whole blood and bone marrow. The tube 12 includes a top or open end 12a, which is closeable, and a bottom or closed end 12b. The bottom 12b may also be selectively closeable.

Disposed within the tube 12 is a first piston or buoy 14 that is able to move along a central axis A of the tube 12. The buoy 14 is generally nearer the bottom end 12b of the tube 12 rather than the open end 12a. Also disposed within the tube 12 is a second piston or plunger 16. The plunger 16 is also able to move within the tube 12 generally between a position closer to the open end 12a to a position closer to the closed end 12b of the tube 12. A cap 18 substantially mates with the open end 12a of the tube 12 to close the tube 12 save for ports formed in the cap 18. Extending from the cap 18 is a plasma valve or port 20 that communicates with an area, described further herein, within the tube 12 defined between the plunger 16 and the cap 18. It will be understood that the plasma port 20 is merely exemplary in nature and simply allows for removal of a selected fraction of a sample, such as plasma from whole blood.

The cap 18 also includes a depth gage port 19. Extending from the plunger 16 and through the depth gage port 19 is a first plunger port 22. A depth guide or gage 24 includes a female connector 26 adapted to connect with the first plunger port 22. The depth gage 24 also includes a depth gage housing or cannula 28. The depth gage housing 28 defines a depth gage bore 30. Incorporated in the housing 28 and extending distal from the end mating with the plunger is a neck 32. The neck 32 includes external neck threads 34. The external neck threads 34 are adapted to engage appropriate internal threads of a mating member.

The mating member may include a compression nut 36 that mates with the external neck threads 34 to lock a depth gage rod 38 in a predetermined position. A split bushing 39 is also provided to substantially seal the depth gage housing 28 when the depth gage rod 38 is locked in place. The depth gage rod 38 extends through the depth gage housing 28 and terminates at a rod handle 40. The rod handle 40 may be a form easily manipulated by a human operator. The rod 38 extends coaxially with axis A of the tube 12. The depth gage rod 38 extends through the plunger 16 a predetermined distance and may be locked at that distance with the compression nut 36.

Although the tube 12 is described here as a cylinder, it will be understood that other shapes may be used, such as polygons. The internal portions, such as the cap 18, buoy 14, and plunger 16, would also include this alternate shape. Preferably the tube 12 is formed of a thermal plastic material which is flexible under the forces required to separate blood. The tube 12 may be made of a material that includes the properties of both lipid and alcohol resistance. These properties help increase the separation speed and decrease the amount of material which may cling to the tube wall 42. For example, CYROLITE® MED2 multipolymer material including acrylic produced by Cyro Industries of Rockaway, N.J. may be used to produce the tube 12.

The tube 12 has a tube wall 42 with a thickness of between about 0.01 millimeters and about 30.0 millimeters, although the tube wall 42 may be any appropriate thickness. The thickness of the tube wall 42 allows the tube wall 42 to flex during the centrifuge process yet be rigid enough for further processing of a blood sample disposed in the tube 12. The tube 12 is closed at the bottom end 12b with a tube bottom 44 formed of the same material as the tube wall 42 and is formed integrally therewith. Generally the tube bottom 44 has a thickness which is substantially rigid under the forces required to separate the sample such that it does not flex.

The buoy 14 includes an upper or collection face 46 that defines an inverse cone or concave surface. Generally the cone has an angle of between about 0.5° to about 45°, and may be about 0.5° to about 90° from a vertical axis, wherein the apex of the cone is within the buoy 14. The collection face 46 forms a depression in the buoy 14 which collects and concentrates material during the separation process. Additionally, the buoy 14 has a bottom face 48 that defines an inverse cone, dome, or covered surface. The buoy bottom face 48 includes an apex 50 that engages the tube bottom 44 before a buoy edge 52 engages the tube bottom 44. The buoy 14 includes a material that is a substantially rigid such that the buoy edges 52 never meet the tube bottom 44. Therefore, there is a gap or free space 54 formed between the buoy edge 52 and the tube bottom 44 along the perimeter of the buoy 14.

The separator 10 is generally provided to separate a multi-component fluid that generally includes various components or constituents of varying densities that are co-mingled or mixed together. The separator 10 includes the buoy 14 that is of a selected density depending upon a selected constituent of the multi-constituent liquid. Although the buoy 14 may be tuned or of any selected density, the following example relates to separation of whole blood to various components. Therefore, the buoy 14 will be discussed to include a selected density relative to whole blood separation. It will be understood, however, that the buoy 14 may be of any appropriate density depending upon the multi-component fluid being separated.

The buoy 14 may be formed of any appropriate material that may have a selected density. For example, when the separator 10 is to separate blood, the buoy 14 generally has a density which is greater than that of red blood cells in a whole blood sample, but less than the plasma or non-red blood cell fraction of a whole blood sample. For blood, the density of the buoy 14 is generally between about 1.02 g/cc and about 1.09 g/cc.

To achieve the selected density, the buoy 14 may be formed as a composite or multi-piece construction, including a plurality of materials. Particularly, a first or outside portion 56 defines the collection face or surface 46 and the buoy edge 52 and is formed of the same material as the tube 12. The outside portion 56 defines a cup or void into which a plug or insert 58 is placed. The insert 58 has a mass such that the density of the entire buoy 14 is within the selected range, for example the range described above. Generally, a high density polyethylene may be used, but the material and size of the insert 58 may be altered to produce the desired density of the buoy 14. Alternatively, the buoy 14 may be formed of a single suitable material that has a density in the selected range. Nevertheless, the buoy 14 formed unitarily or of a single material would still include the other portions described in conjunction with the buoy 14.

The outside portion 56 of the buoy 14 also defines the outside circumference of the buoy 14. The outside circumference of the buoy 14 is very close to the internal circumference of the tube 12. Due to the operation of the buoy 14, however, described further herein, there is a slight gap between the outside of the buoy 14 and the inside of the tube 12. Generally, this gap is between about 1 and about 10 thousandths of an inch around the entire circumference of the buoy 14. Generally, it is desired that the distance between the outside circumference of the buoy 14 and the inside circumference of the tube 12 is great enough to allow a selected material or component to pass. For example, in whole blood the distance is selected so that red blood cells may pass through the gap without being lysed, damaged, or activated.

The plunger 16 includes a plunger front or collection face 60 and a plunger wall 62 that extends from the plunger front face 60. The plunger wall 62 extends relatively perpendicular to the plunger front face 60 and substantially parallel to the tube wall 42. Extending from the center of the plunger 16 is a sample collection projection 64. Extending from the top of the collection projection 64 is the first plunger port 22. The sample collection projection 64 includes a plunger sample collection bore 68 defined therethrough. The plunger sample collection bore 68 terminates at a sample collection aperture 70 that is substantially in the center of the plunger front face 60. The plunger front face 60 also defines an inverse cone where the sample collection aperture 70 is the apex of the cone. The plunger front face 60 defines a cone with an angle substantially similar or complementary to the collection face 46 of the buoy 14. In this way, the plunger front face 60 may mate substantially completely with the collection face 46 for reasons described more fully herein.

The plunger 16 also includes a back face 72. Extending from the plunger front face 60 to the back face 72 is a bore 74. A check valve 76 is operably connected to the bore 74. The check valve 76 allows a liquid to move from the plunger front face 60 to the back face 72 while not allowing the liquid to move from the back face 72 to the plunger front face 60. Therefore, the check valve 76 is substantially a one-way valve which allows a material to move in only one direction. The check valve 76 may also operate automatically allowing flow in only one predetermined direction. Alternatively, the check valve 76 may be operated manually and include a portion extending from the check valve 76 requiring manipulation to stop or start a flow through the check valve 76.

The plunger 16 may be made out of any appropriate material which does not interfere with the separation of the fractions of the fluid, such as whole blood. The plunger 16, however, is made of a material that is flexible or at least partially deformable. A flexible material allows the plunger 16 to have an external circumference defined by the plunger walls 62 that is substantially equal to the internal circumference of the tube 12. Because of the deformability of the plunger 16, however, the plunger 16 is still able to move within the tube 12. The plunger 16 is able to move through the tube 12 and also substantially wipe the interior of the tube wall 42. This creates, generally, a moveable seal within the tube 12. Thus, substantially no material escapes the action of the separator 10 when the plunger 16 is plunged into the tube 12. This also helps concentrate the portion of the sample desired to be collected, described more fully herein.

The cap 18 provides a structure to substantially close the tube 12. The cap 18 particularly includes a plate 78 that has an external circumference substantially equal to the external circumference of the tube 12. Extending from the plate 78 and into the tube 12 is a flange 80. The external circumference of the flange 80 is substantially equal to the internal circumference of the tube 12. In this way, the cap 18 substantially closes the tube 12. It will be understood the cap 18 may be in any form so long as the cap 18 substantially closes and/or seals the tube 12 when installed.

Formed through the center of the plate 78 is the depth gage port 19. The depth gage port 19 is also adapted to receive the sample collection projection 64. The first plunger port 22 extends above the plate 78 through the depth gage port 19. The circumference of the depth gage port 19 is substantially equal to the external circumference of the sample collection projection 64 such that a liquid seal is formed. The plate 78 defines a sample face 84 that includes an interior side of the cap 18. The area between the sample face 84 of the cap 18 and the back face 72 of the plunger 16 define a plasma collection area 86. Although the plasma collection area 86 is exemplary called the plasma collection area, it will be understood that the plasma collection area 86 may also collect any appropriate fraction of the sample that is positioned within a separator 10. The plasma collection area 86 is merely an exemplary name and an example of what material may be collected in the area of the separator 10. As discussed herein, the separator 10 may be used to separate whole blood into various fractions, therefore the plasma collection area 86 is used to collect plasma. The plasma collection area 86 also allows a space for the check valve 76 to be installed.

A second bore 88 is formed in the plate 78. Extending through the second bore 88 is the plasma collection valve 20. In liquid communication with the plasma collection valve 20 is a plasma collection tube 92. The plasma collection tube 92 has a length such that the plasma collection tube 92 is able to extend from the plasma collection valve 20 to substantially the tube bottom 44. The plasma collection tube 92, however, is flexible enough such that it may be folded or compressed to fit within the plasma collection area 86 when the plunger is substantially near the top 12a of the tube 12. The plasma collection tube 92 may also be connected to a hose barb 93 that includes a plasma collection bore 93a. The plasma collection bore 93a is substantially level with the plunger back face 72. Alternatively, the plasma collection bore 93a may be positioned below the plunger back face 72 but in fluid communication with the plasma collection tube 92.

The outboard side of the plasma collection valve 20 may include external threads 94 to mate with internal threads of a plasma valve cap 96. Therefore, the plasma collection valve 20 may be selectively opened and closed via the plasma valve cap 96. It will be understood, however, that other appropriate means may be used to open and close the plasma collection valve 20 such as a clip or a plug. It will be understood that the plasma collection valve 20, plasma collection tube 92, plasma collection bore 88 may be used to collect any appropriate material or fraction from the separator 10.

Also formed in the plate 78 is a vent bore 98. The vent bore 98 allows air to flow into the collection area 86 as the plunger 16 is being plunged into the tube 12. The vent bore 98 may include a filter 100 such that liquid cannot escape from the tube 12. The filter 100 allows air to enter or escape from the collection area 86 while maintaining the liquid seal of the tube 12 produced by the cap 18.

Selectively attachable to the first plunger port 22 is the depth gage 24. The female connector 26 interconnects the depth gage housing 28 to the first plunger port 22. Internal threads in the female connector 26 mate with an external thread 102 formed on the first plunger port 22. It will be understood, however, that other engagement mechanisms between the depth gage 24 and the plunger 16 may be used. For example, a snap connection rather than a threaded connection between the two may be used.

The depth gage housing 28 is formed to be substantially rigid. Suitable materials, when sized properly, include polycarbonate and CYROLITE® MED2 multipolymer material including acrylic. The material preferably is both rigid and does not substantially react with the sample. It is rigid enough to provide a mechanism to plunge the plunger 16 into the tube 12. In addition the external circumference of the depth gage housing 28 is substantially equal to the circumference of the depth gage port 19 in the plate 78. Therefore, as the plunger 16 is being plunged into the tube 12 with the depth gage 24, no liquid material is allowed to escape around the depth gage housing 28 and through depth gage port 19.

Formed within the depth gage housing 28 is the bore 30 which receives the depth gage rod 38. The depth gage rod 38 extends through the sample collection bore 68 of the sample collection projection 64 and protrudes through the sample collection aperture 70 a predetermined length. The depth gage rod 38 extends through the sample collection aperture 70 a length such that when an end 104 of the depth gage rod 38 meets the buoy 14, the volume defined by the collection face 46 and the plunger front face 60 is between about 5 percent and about 30 percent of the total volume of the sample that the tube 12 holds. The projection of the depth gage rod 38 allows for an easily reproducible collection amount and concentration over several trials.

The compression nut 36 locks the depth gage rod 38 in the predetermined position. Nevertheless, once the plunger 16 has been plunged to the desired depth in the tube 12, the compression nut 36 may be loosened so that the depth gage rod 38 may be removed from the plunger 16 and the depth gage housing 28 without moving the plunger 16. A syringe or other appropriate device may then be affixed to the external neck threads 34 of the depth gage 24 to extract the fraction or phase that is between the plunger front face 60 and the collection face 46. As described further herein, the fraction or phase that is left between the plunger front face 60 and the collection face 46 may be the buffy coat of a whole blood sample. Nevertheless, it will be understood that the fraction between the plunger front face 60 and the collection face 46 may be any appropriate fraction of the sample that is disposed in the separator 10.

Figure 4:
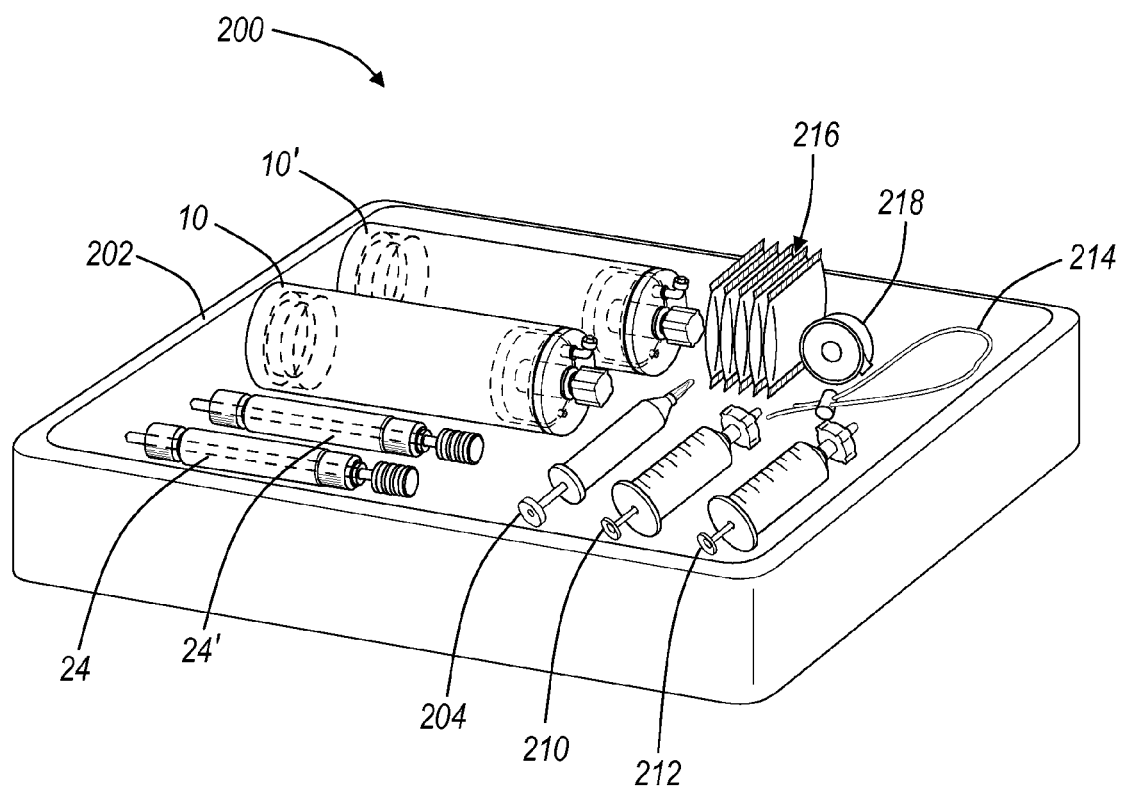
FIG. 4 is a kit including the separator according to an embodiment of the present invention.

The separator 10 may be provided alone or in a kit 200, as illustrated in FIG. 4. The kit 200 may be placed in a tray 202 which is covered to provide a clean or sterile environment for the contents of the kit 200. The kit 200 may include at least a first separator 10 and a second separator 10'. A first depth gage 24 and a second depth gage 24' are also provided, one for each separator 10, 10'. The kit 200 also generally includes a first syringe 204, including a needle, to draw a biological sample, such as blood from a patient. The first syringe 204 may also be used to place the sample in the first separator 10. After centrifuging the sample a second device or syringe 210 may be used to extract a first fraction of the sample. While a third device or syringe 212 may be used to extract a second fraction of the sample. Also a tourniquet 214 and other medical supplies, such as gauze 216 and tape 218, may be provided to assist the practitioner. It will be understood the elements of the kit 200 are merely exemplary and other appropriate items or elements may be included.

With reference to FIGS. 5A-5D a method using the blood separator 10 is illustrated. The following example relates specifically to the taking and separation of a sample of whole blood from a patient. Nevertheless, it will be understood that another appropriate biological material may be separated and concentrated using the separator 10. For example, bone marrow may be separated and concentrated using the separator 10. The various fractions of the bone marrow are similar to the fractions of whole blood. Generally, the bone marrow includes a fraction that includes substantially dense material and a second phase that is less dense and has other components suspended therein, such as nucleated cells. The bone marrow sample may be positioned in the separator 10, similarly to the whole blood as described herein, and separated in a substantially similar manner as the whole blood. The separator 10 can then be used to remove nucleated cells from the bone marrow sample whereas the separator 10, as described herein, is used to remove the buffy coat from the whole blood which includes platelets and other appropriate materials.

A mixture of whole blood and bone marrow may be positioned in the separator 10 for separation and concentration. Similar methods and steps will be used to separate the mixture of whole blood and bone marrow with a main difference being the material that is separated. It will also be understood that various centrifuge times or forces may be altered depending upon the exact material that is being separated with the separator 10. It will also be understood that the separation of whole blood, bone marrow, or a mixture of whole blood and bone marrow are merely exemplary of the materials that may be separated using the separator 10.

With reference to FIGS. 5A-5D and to a whole blood sample, a sample of whole blood taken from a patient is placed in the tube 12 with an anticoagulant using the first syringe 204 or other appropriate delivery method. In particular, the first syringe 204 may be connected to the first plunger port 22. After which the blood sample is provided to the tube 12 via the sample collection bore 68 and sample collection aperture 70. A cap 220 is then placed over the first plunger port 22 to substantially seal the tube 12.

After the whole blood sample is delivered to the tube 12, the separator 10 is placed in a centrifuge. The second separator 10', substantially identical to the first, is placed opposite the first separator 10 including the sample in a centrifuge. The second separator 10' may also include a second sample or may include a blank, such as water, so that the centrifuge is balanced. The second separator 10' balances the centrifuge, both by weight and dynamics.

The separator 10 is then spun in the centrifuge in a range between about 1,000 and about 8,000 RPMs. This produces a force between about 65 and about 4500 times greater than the force of normal gravity, as generally calculated in the art, on the separator 10 and the blood sample placed in the separator 10. At this force, the more dense material in a whole blood sample is forced towards the bottom 12b of the tube 12. The dense material, such as red blood cells or a red blood cell fraction 222, collects on the tube bottom 44. Because the buoy 14 has a density that is less than the red blood cell fraction 222, it is forced in a direction toward the top 12a of the tube 12 in the centrifuge. Nevertheless, because the buoy 14 is denser than a plasma fraction 224, the buoy 14 does not reach the top 12a of the tube 12.

The forces also affect the tube wall 42. The forces compress the tube 12 linearly along axis A thereby bowing or flexing the tube wall 42. As the tube wall 42 compresses it increases the diameter of the tube 12 making it easier for the buoy 14 to move in the direction of the top 12a of the tube 12. In addition, the bottom face 48, defining an inverse cone, helps the initial movement of the buoy 14. Because the buoy 14 is not substantially flat along its bottom, it does not form a vacuum interaction with the tube bottom 44. Therefore, the initial movement of the buoy 14 away from the tube bottom 44 is quicker than if the bottom of the buoy 14 was flat.

During the centrifuge process the red bloods cells of the red blood cell fraction 222 force the buoy 14 in the direction of the top 12a of the tube 12 because the buoy 14 is less dense than the red blood cell fraction 222. Although the whole blood sample, including the red blood cells is loaded above the buoy 14, the red blood cells are able to move between the buoy 14 and the tube wall 42 because the circumference of the buoy 14 is less than the internal circumference of the tube 12. During the centrifuge process the buoy 14 stops at an interface of a plasma fraction 224 and the red blood cell fraction 222 because of the selected or tuned density of the buoy 14.

Figure 5A:
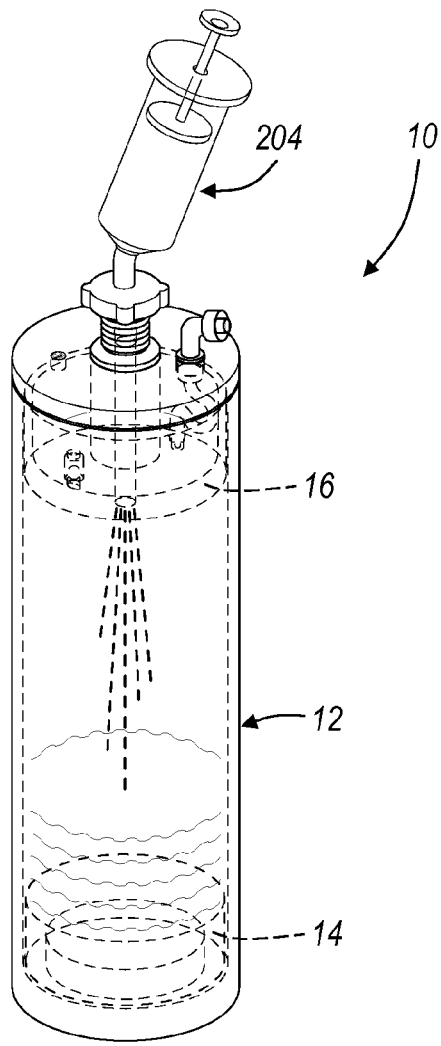
FIG. 5A is a plan view of the separator being filled.
Figure 5B:
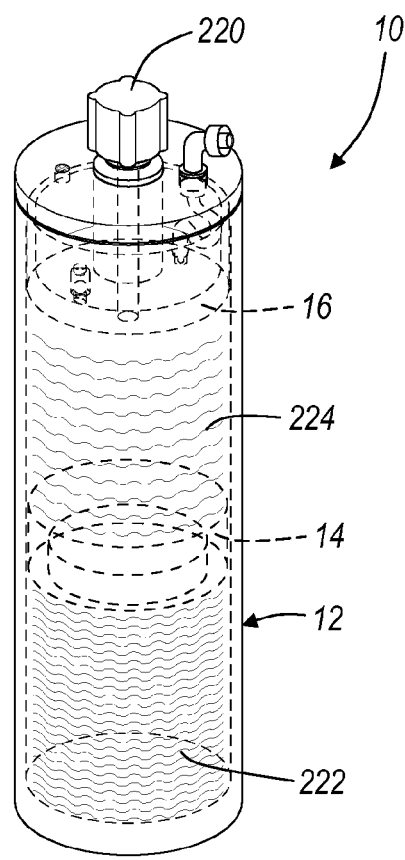
FIG. 5B is a plan view of a blood sample in the separator after the centrifuge process.

With particular reference to FIG. 5B, the centrifuge process has been completed and the buoy 14 has moved to the interface of the red blood cell fraction 222 and plasma fraction 224. After the centrifuge has slowed or stopped, and before or after the tube 12 has been removed from the centrifuge, the tube wall 42 decompresses which helps support the buoy 14 at the interface position. It is also understood that applying an external pressure to the tube 12 via fingers or another apparatus may help stabilize the buoy 14 during the plunging procedure described herein.

On or near collection face 46 is a third fraction 226 including a small, yet concentrated, amount of red blood cells, white blood cells, platelets, and a substantial portion of a buffy coat of the blood sample. Although the plasma is also present near the collection face 46 at this point the solid portions of the buffy coat are more compressed against the collection face 46. The position of the buoy 14 also helps in this matter. Because the buoy 14 is a single body it defines the interface of the plasma traction 224 and the red blood cell fraction 222. Also the density of the buoy 14 assures that it has not passed into the plasma fraction 224. Therefore, the fractions remain separated after the centrifuge process. In addition because the buoy 14 is tuned to the density of the red blood cell fraction 222, it is not affected by variations in the density of the plasma fraction 224 and the buoy's 14 position is always at the interface of the red blood cell fraction 222 and the plasma fraction 224.

Figure 5C:
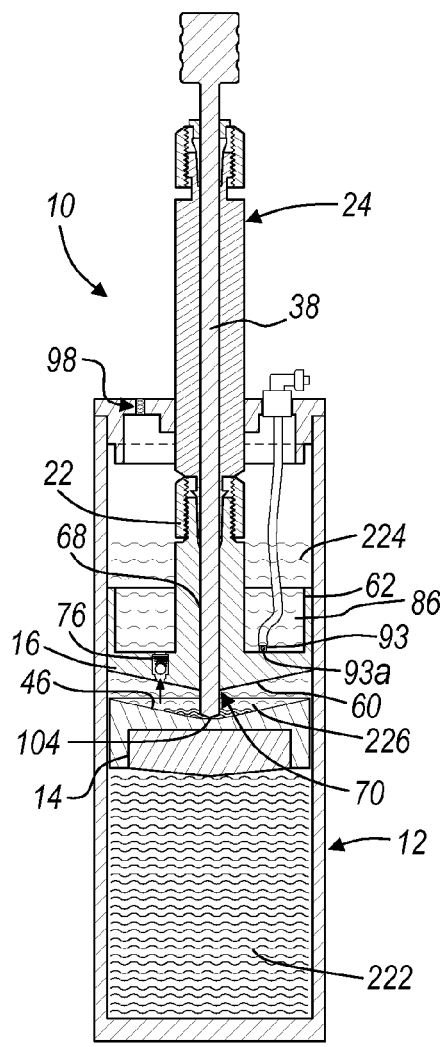
FIG. 5C is a plan view of the plunger plunged into the tube with the depth gage to further separate the blood sample.

With particular reference to FIG. 5C, the depth gage 24 is affixed to the first plunger port 22 of the sample collection projection 64. After connecting the depth gage 24 to the first plunger port 22, the plunger 16 is plunged into the tube 12 by pushing on the depth gage 24. As this is performed the plasma fraction 224, formed and separated above the buoy 14, is able to flow through the check valve 76 into the plasma collection area 86. This displacement of the plasma fraction 224 allows the plunger 16 to be plunged into the tube 12 containing the blood sample.

The plunger 16 is plunged into the tube 12 until the point where the end 104 of the depth gage rod 38 reaches the buoy 14. The volume left in the collection face 46 is the third fraction 226 and is determined by the depth gage 24. It may be adjusted by selectively determining the amount that the depth gage rod 38 extends below the plunger front face 60. By adjusting the depth gage 24, the concentration of the third fraction 226 can be adjusted depending upon the desires of the operator.

The plasma fraction 224 is held in the plasma collection area 86 for later withdrawal. Therefore, the use of the plunger 16 and the buoy 14 creates three distinct fractions that may be removed from the tube 12 after only one spin procedure. The fractions include the red blood cell fraction 222, held between the buoy 14 and the tube bottom 44. The third or buffy coat fraction 226 is held between the plunger 16 and the buoy 14. Finally, the plasma fraction 224 is collected in the plasma collection area 86.

Figure 5D:
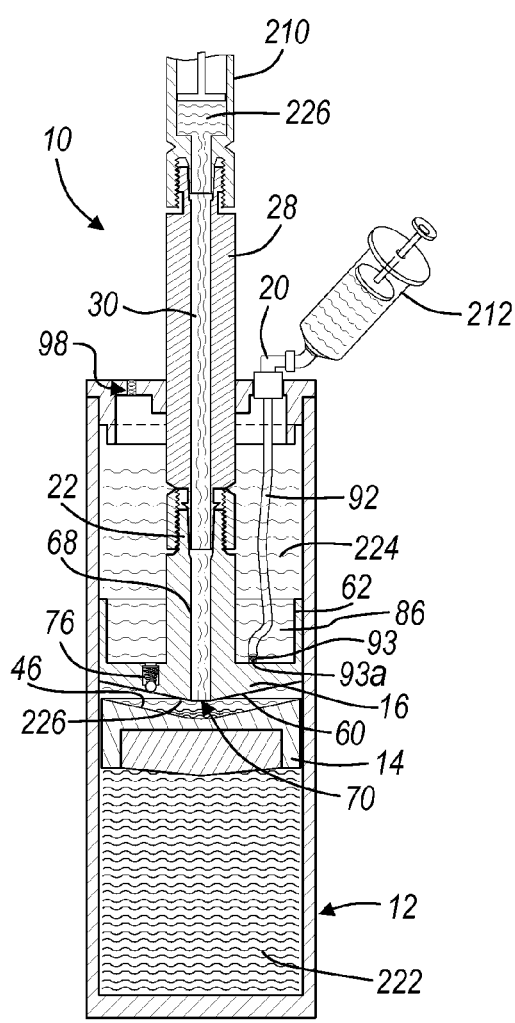
FIG. 5D is a plan view of the buffy coat and the plasma fractions being extracted from the separator.

The third fraction 226 may be extracted from the tube 12 first, without comingling the other fractions, through the sample collection bore 68. With particular reference to FIG. 5D, the depth gage rod 38 may be removed from the depth gage housing 28. This creates a sample collection cannula which includes the depth gage bore 30, the sample collection bore 68, and the sample collection aperture 70. After the depth gage rod 38 has been removed, the second syringe 210 may be affixed to the depth gage housing 28 via the external neck threads 34. The second syringe 210 may be substantially similar to the first syringe 204.

Before attempting to withdraw the third fraction 226 the separator 10 may be agitated to re-suspend of the platelets and concentrated red blood cells in a portion of the plasma remaining in the collection face 46. This allows for easier and more complete removal of the third fraction 226 because it is suspended rather than compressed against the collection face 46. A vacuum is then created in the second syringe 210 by pulling back the plunger to draw the third fraction 226 into the second syringe 210.

As the third fraction 226 is drawn into the second syringe 210 the plunger 16 moves towards the buoy 14. This action is allowed because of the vent bore 98 formed in the cap 18. Atmospheric air is transferred to the plasma collection area 86 through the vent bore 98 to allow the third fraction 226 to be removed. This also allows the movement of the plunger 16 towards the buoy 14. This action also allows the plunger 16 to "wipe" the collection face 46. As the plunger front face 60 mates with the collection area 46 the third fraction 226 is pushed into the sample collection aperture 70. This ensures that substantially the entire third fraction 226 collected in the collection area 46 is removed into the second syringe 210. It can also increases the repeatability of the collection volumes. In addition, because the second syringe 210 does not protrude out the sample collection aperture 70, it does not interfere with the collection of the third fraction 226. Once the plunger front face 60 has mated with the collection face 46 there is substantially no volume between the plunger 16 and the buoy 14.

Once the third fraction 226 is extracted the second syringe 210 is removed from the first plunger port 22. Also the extraction of the third fraction 226 leaves the plasma fraction 224 and the red blood cell fractions 222 separated in the tube 12. At this point a third syringe 212 may be affixed to the plasma collection valve 20. The third syringe 212 is connected to the external threads 94 of the plasma collection valve 20 to ensure a liquid tight connection. It will be understood, however, that another connection mechanism such as a snap or compression engagement may be used to connect the third syringe 212 to the plasma collection valve 20.

A vacuum is then created in the third syringe 212 to draw the plasma fraction 224 from the plasma collection area 86 through the plasma collection tube 92. As discussed above, the plasma collection tube 92 is connected to the hose barb 93. Therefore, the plasma flows through the plasma collection bore 93a through the hose barb 93, and then through the plasma collection tube 92. It will be understood that the plasma collection tube 92 may alternatively simply rest on the plunger back face 72 to collect the plasma fraction 224. In this way the plasma fraction 224 may be removed from the blood separator 10 without comingling it with the red blood cell fraction 222. After the plasma fraction 224 is removed, the separator 10 may be dismantled to remove the red blood cell fraction 222. Alternatively, the separator 10 may be discarded in an appropriate manner while retaining the red blood cell fraction 222.

The separator 10 allows for the collection of three of a whole blood sample's fractions with only one centrifugation spin. The interaction of the buoy 14 and the plunger 16 allows a collection of at least 40% of the available buffy coat in the whole blood sample after a centrifuge processing time of about 5 minutes to about 15 minutes. The complementary geometry of the plunger front face 60 and the collection face 46 help increase the collection efficiency. Although only the cone geometry is discussed herein, it will be understood that various other geometries may be used with similar results.

The plunger front face 60 being flexible also helps ensure a complete mating with the collection face 46. This, in turn, helps ensure that substantially the entire volume between the two is evacuated. The process first begins with the suction withdrawal of the third fraction 226 via the second syringe 210, but is completed with a fluid force action of the third fraction 226 as the plunger front face 60 mates with the collection face 46. As the plunger front face 60 mates with the collection face 46 the fluid force assists in removal of the selected fraction.

The plunger 16 also substantially wipes the tube wall 42. Because the plunger 16 is formed of a flexible material it forms a seal with the tube wall 42 which is movable. Therefore, substantially no liquid is able to move between the plunger wall 62 and the tube wall 42. Material is substantially only able to go past the plunger front face 60 via the check valve 76.

The complementary geometry also helps decrease the collection time of the third fraction 226. Therefore, entire time to prepare and remove the third fraction 226 is generally about 5 to about 40 minutes. This efficiency is also assisted by the fact that the separator 10 allows for the removal of the third fraction 226 without first removing the plasma fraction 224, which includes the buffy coat, and respinning the plasma fraction 224. Rather one spin in the separator 10 with the whole blood sample allows for the separation of the buffy coat for easy extraction through the plunger 16.

As discussed above, the separator 10 may be used to separate any appropriate multi-component material. For example, a bone marrow sample may be placed in the separator 10 to be centrifuged and separated using the separator 10. The bone marrow sample may include several fractions or components that are similar to whole blood fractions or may differ therefrom. Therefore, the buoy 14 may be altered to include a selected density that is dependent upon a density of a selected fraction of the bone marrow. The bone marrow may include a selected fraction that has a different density than another fraction and the buoy 14 may be designed to move to an interface between the two fractions to allow for a physical separation thereof. Similar to the whole blood fraction, the plunger 16 may then be moved to near a collection face 46 of the buoy 14. The fraction that is then defined by the collection face 46 and the plunger 16 may be withdrawn, as described for the removal of the buffy coat from the whole blood sample. For example, the middle fraction or third fraction in the bone marrow sample may include a fraction of undifferentiated or stem cells.

It will also be understood that mixtures of various fluids may be separated in the separator 10. For example, a mixture of whole blood and bone marrow may be positioned in the separator 10 at a single time. The buoy 14 may be tuned to move to an interface that will allow for easy removal of both the buffy coat, from the whole blood sample, and the undifferentiated cells, from the bone marrow sample. Nevertheless, it will be understood that the separator 10 may be used within any appropriate biological material or other material having multiple fractions or components therein. Simply, the buoy 14 may be tuned to the appropriate density and the plunger 16 may be used to cooperate with the buoy 14 to remove a selected fraction.

Figure 6A:
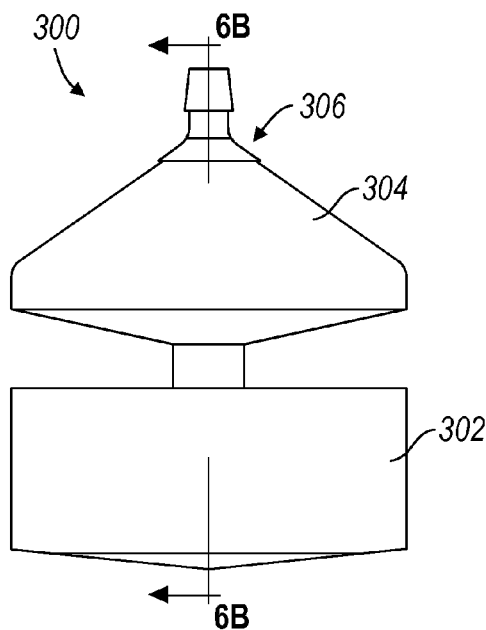
FIG. 6A is a side plan view of a buoy system according to various embodiments.
Figure 6B:
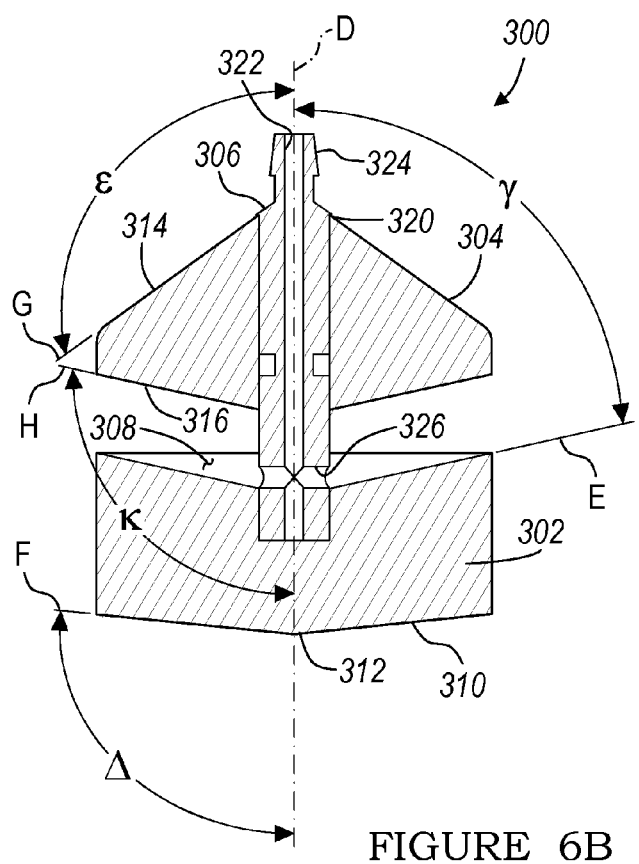

With reference to FIGS. 6A and 6B, a buoy system 300 is illustrated. The buoy system 300 generally includes a first buoy or fraction separator member 302 and a second buoy member or fraction separator 304. The first buoy 302 and the second buoy 304 may be operably interconnected with a buoy system cylinder or member 306. The buoy system 300 may be placed in a tube, such as the tube 12. The tube 12 may be formed of any appropriate material, such as the CYROLITE® MED2 multipolymer material including acrylic as discussed above. Nevertheless, the buoy system 300 may be designed to fit in the tube 12 or may be formed to fit in any appropriate member that may be disposed within a selected centrifuging device. It will be understood that the following discussion relating to buoy system 300 to be substantially matched to the size of the tube 12 is merely exemplary. As the buoy 14 may be sized to fit in any appropriate tube, the buoy system 300 may also be sized to fit in any appropriate tube. It will be further understood that the tube 12 may be any appropriate shape. The tube 12 need not only be cylindrical but may also be or include conical portions, polygonal portions, or any other appropriate shapes.

The first buoy 302 of the buoy system 300 may be generally similar in geometry to the buoy 14. It will be understood that the first buoy member 302 may be formed in the appropriate manner including shape or size to achieve selected results. Nevertheless, the first buoy member 302 generally includes an exterior diameter that may be slightly smaller than the interior diameter of the tube 12. Therefore, the first buoy member 302 may be able to move within the tube 12 during the centrifugal process. Also, as discussed above, the tube 12 may flex slightly during the centrifuging process, thus allowing the first buoy member 302 to include an exterior diameter substantially equivalent to the interior diameter of the tube 12. As discussed further herein, during the centrifugation process, a portion of the fraction of a sample may pass between the exterior wall of the first buoy member 302 and the tube 12.

The first buoy member 302 may generally include a density that is substantially equivalent to a first or selected fraction of the sample. If the sample to be separated includes whole blood and is desired to separate the red blood cells from the other portions of the sample, the first buoy member 302 may have a selected density that may be about 1.00 grams per cc (g/cc) to about 1.10 g/cc. It will be understood that the density of the first buoy member 302 may be any appropriate density, depending upon the fraction to be separated, and this range of densities is merely exemplary for separating red blood cells from a whole blood sample.

In addition, the first buoy member 302 includes a collection face or area 308 at a proximal or upper portion of the first buoy member 302. The collection face 308 generally defines a concave area of the first buoy member 302 and may have a selected angle of concavity. The buoy assembly 300 defines a central axis D. The collection face 308 defines a surface E that is formed at an angle $\gamma$ to the central axis D of the buoy system 300. The angle $\gamma$ may be any appropriate angle and may be about 0.5° to about 90°. The angle $\gamma$ may, however, be between about 45° and 89.5°. Nevertheless, it will be understood that the angle $\gamma$ may be any appropriate angle to assist in collection of a selected fraction or portion of the sample by the first buoy member 302.

A bottom or lower surface 310 of the first buoy member 302 may define a bottom face. The bottom face 310 may also be formed at an angle D relative to the central axis D. The bottom surface 310 defines a surface or plane F that may be formed at an angle $\Delta$ relative to the central axis D of the buoy system 300. The angle $\Delta$ may be any appropriate angle and may be about 90° to about 160°. For example, the angle $\Delta$ may be about 15°. Similarly to the buoy bottom face 48, the bottom surface 310 defines an apex 312 that may first engage the bottom 12d of the tube 12, such that most or the majority of the bottom surface 310 does not engage the tube 12. As illustrated further herein, the apex 312 allows for a free space or gap to be formed between the bottom face 310 of the first buoy member 302 and the bottom 12b of the tube 12.

The second buoy member 304 may include an outer diameter substantially equivalent to the outer diameter of the first buoy member 302. Therefore, the second buoy 304 may move with the first buoy 302, particularly if the second buoy 304 is interconnected with the first buoy 302 with the buoy central cylinder 306. Nevertheless, the second buoy member 304 may be allowed to move substantially freely within the tube 12 during the centrifuging process.

The second buoy member 304 also includes an upper or superior surface 314 that defines a plane G that is formed at an angle relative to the central axis D of the buoy system 300. The angle c of the plane G relative to the central axis D of the buoy system 300 may be any appropriate angle. For example, the angle $\epsilon$ may be about 90° to about 150°. Generally, the angle $\epsilon$ may assist in allowing a selected fraction or a portion of the sample to pass over the top surface 314 and past the second buoy member 304 during the centrifuging process.

The second buoy member 304 also define a bottom or inferior surface 316 that also defines a plane H that may be formed at an angle K relative to the central axis D of the buoy system 300. The angle K may be any appropriate angle, such as about 90° to about 150°. Nevertheless, the angle K may be substantially complementary to the angle $\gamma$ of the collection face 308 of the first buoy member 302. For example, if the angle $\gamma$ is about 80°, the angle K may be about 100°, such that substantially 180° or a straight line is formed when the first buoy member 302 engages the second buoy member 304. This may be for any appropriate reason, such as extraction of a fraction that may be disposed near the collection face 308 of the first buoy member 302. Nevertheless, the angle K may be any appropriate angle as the angle $\gamma$.

The second buoy member 304 may be formed to include any appropriate density. For example, the second buoy member 304 may include a density that is less than the plasma fraction of a whole blood sample. It will be understood that the second buoy member 304 may include any appropriate density and a density that is less than the plasma fraction of a whole blood sample is merely exemplary. Nevertheless, if a whole blood sample is desired to be separated and the plasma sample is to be substantially separated from another fraction, the second buoy member 304 may include a density that is less than the plasma fraction of the whole blood sample. Therefore, the density of the second buoy member 304 may be about 0.01 g/cc to about 1.03 g/cc. As described herein, if the second buoy member 304 includes a density less than the plasma fraction of a whole blood sample and the first buoy member 302 includes a density greater than that of the red blood cells, the buoy system 300 may be substantially positioned near an interface between the red blood cell fraction and the plasma fraction of a whole blood sample. Therefore, as discussed above, and further described herein, the platelet or buffy coat fraction of the whole blood sample may be substantially collected near or in the collection face 308 of the buoy system 300.

The buoy post 306 may operably interconnect the first buoy member 302 and the second buoy member 304. The buoy post 306 may be any appropriate connection member. The buoy post need not be a single cylindrical portion. For example the buoy post 306 may include one or more members interconnecting the first buoy member 302 and the second buoy member 304, such as around a perimeter thereof. In addition, the buoy post 306 may include any appropriate shape or geometry.

The buoy system post 306 may be rigidly affixed to the first buoy member 302 and the second buoy member 304, such that the first buoy member 302 may not move relative to the second buoy member 304 and vice versa. Alternatively, the buoy post 306 may be slidably connected to either or both the first buoy member 302 and the second buoy member 304. According to various embodiments, the buoy post 306 is generally fixedly connected to the first buoy member 302 and slidably interconnected to the second buoy member 304. The buoy post 306 may include a catch portion or lip 320 that is able to engage a portion of the second buoy member 304, such that a range of travel of the second buoy member 304, relative to the first buoy member 302 is limited. Nevertheless, the range of travel of the second buoy member 304 towards the first buoy member 302 may be substantially unlimited until the second buoy member 304 engages the first buoy member 302.

The buoy post 306 may also define a central cannula or bore 322. The post bore 322 may include a connection portion 324 substantially defined near an upper or a proximal end of the buoy post 306. This may allow for interconnection of various components with the buoy post 306, such that various components may be moved through the bore 322 from an exterior location. The buoy post 306 may also define a port or cannula 326 that connects the post cannula 322 with the collection face 308. Therefore, a substance may travel through the post cannula 322 and through the port 326. Various substances may then be provided to or removed from the collection face 308 of the first buoy member 302.

The buoy system 300 may be used to separate a selected multi component sample, such as a whole blood sample. With continuing reference to FIGS. 6A and 6B, and reference to FIGS. 7A-7D, a method of using the buoy system 300, according to various embodiments, is illustrated and described. With reference to FIGS. 7A-7D, like reference numerals are used to indicate like portions of the tube 12 and the associated mechanisms described in FIGS. 1-3. Therefore, it will be understood that the buoy system 300 may be used with the tube 12 or any other appropriate tube or container system or apparatus. Nevertheless, for simplicity, the description of a method of use of the buoy system 300 will be described in conjunction with the tube 12.

The tube 12 may include the cap 18 that further defines a plasma valve or port 20. Extending through the cap 18 and interconnecting with a first flexible tube or member 92, the plasma port 20 may be used to extract a selected fraction of the sample that is positioned above the second buoy member 304. As illustrated above, the first tube 92 may also be interconnected with a selected portion of the system, such as the top surface 314 of the second buoy member 304. As illustrated above, a valve may be positioned and is operably interconnect the tube 92 with the upper surface 314 of the second buoy member 304. Nevertheless, such a valve is not necessary and it may be provided merely for convenience.

Other portions of the blood separator system 20, particularly those portions of the tube 12 and the cap 18 that have various valves connected therewith may be included in the tube 12 and used with the buoy system 300. Nevertheless, once the buoy system 300 is interconnected, it may be positioned in the interior of the tube 12 and the syringe 204 used to place a sample into the tube 12. The sample may be expressed from the syringe 204 into the interior of the tube 12 and the sample may be any appropriate sample, such as a whole blood sample. Nevertheless, it will be understood, such as discussed above, various other samples may be used, such as bone marrow samples, a mixture of bone marrow and whole blood or nonbiological fluids or materials. It will be understood that two buoys 302 and 304 may generally be near one another when the sample is positioned in the tube 12, but are illustrated apart for clarity of the present discussion.

Also, the sample may be placed in the tube 12 according to various methods. As described above, an anticoagulant or other components may be mixed with the whole blood sample, if a whole blood sample is used, before the whole blood sample is positioned within the tube 12. The syringe 204 is connected with the plunger port 22 extending from the cap 18, although a plunger may not be used in various embodiments.

After the sample is positioned within the tube 12, as described above, a cap may be positioned over the port 22, such that the sample is not allowed to escape from the tube 12.

After the sample is placed in the tube 12 and the cap placed on the port 22, the tube 12 including the sample and the buoy system 300 may be centrifuged.

With reference to FIG. 7B, after a centrifugation of the tube 12, including the buoy system 300, substantially three fractions of the sample may be formed. A first fraction 330 may be positioned between the bottom face 310 and the bottom of the tube 44. A second fraction may be positioned between the collection face 308 and the bottom surface 316 of the second buoy 304. In addition, a third fraction may be positioned between the upper surface 314 and the cap 18 of the tube 12. Generally, the first fraction 330, the second fraction 332, and the third fraction 334 are substantially physically separated with the buoy system 300. During the centrifugation process, the tube 12 may flex slightly to allow for ease of movement of the buoy system 300 through the tube 12 and the sample. Nevertheless, the buoy system 300, during the centrifugation process, substantially creates the three fractions 330, 332, and 334 without the operation of an operator. Therefore, the formation of at least three fractions may be substantially simultaneous and automatic using the buoy system 300.

The buoy system 300 substantially separates the fractions 330, 332, and 334, such that they may be easily removed from the tube 12. For example, with reference to FIG. 7C, a syringe or other instrument 340 may be used to extract the second fraction 332 by interconnecting a cannula or bored tube 342 with the connection portion 324 of the buoy cylinder 306. By drawing the plunger 344 into the extraction syringe 340, a vacuum or upward force is produced within the extraction syringe 340. This force draws the second fraction 332 through the ports 326 of the buoy post 306 and through the buoy cannula 322. Therefore, the second fraction 332 may be extracted from the tube 12 without substantially comingling the second fraction 332 with either the first fraction 330 or the third fraction 334. The second fraction 332 is drawn in the direction of arrow M through the cannula 322 and into the extraction syringe 340.

Alternatively, if the post 306 is not provided other portions may be provided to gain access to the second fraction 332. For example, if a plurality of members are provided around the perimeter of the first buoy 302 and the second buoy 304 a valve portion, such as a puncture-able valve, may be provided in the second buoy 304 to be punctured with an object. In this way an extraction needle may puncture the valve to gain access to the second fraction 332. Regardless, it will be understood that the buoy system 300 may be able to form a plurality of fractions, such as the three fractions 330, 332, and 334 and at least the second fraction 332 may be extracted without substantially comingling the various fractions.

During the extraction of the second fraction 332 through the cannula 322, the second buoy member 304 may move in the direction of arrow N towards the first buoy member 302. As described above, the collection face 308 of the first buoy member may include an angle γ that is substantially complementary to the bottom face 316 of the second buoy member 304. Therefore, if the second buoy member 304 is allowed to move along the buoy cylinder 306, the bottom face 316 of the second buoy member 304 may be able to substantially mate with the collection face 308 of the first buoy member 302. Alternatively, if the second buoy member 304 is not allowed to move, the second buoy member may be provided with a vent port or valve, such that the extraction of the second fraction 332 from the collection face 308 may not be hindered by the buildup of undesirable forces. Nevertheless, if the second buoy member 304 may move, the interaction of the bottom face 316 of the second buoy member 304 may assist in substantially removing the entire second fraction 332 from the tube 12. As described above, the bottom face 60 of the plunger 16 may also serve a similar purpose when engaging the collection face 46 of the buoy 14.

Figure 7C:
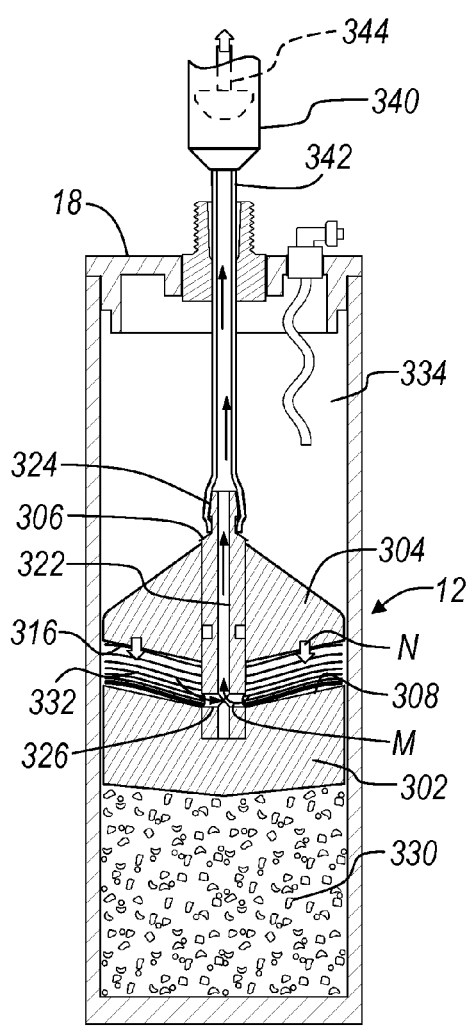
FIG. 7C is a plan view of a separator system being used to extract a selected fraction after the centrifugation process.
Figure 7D:
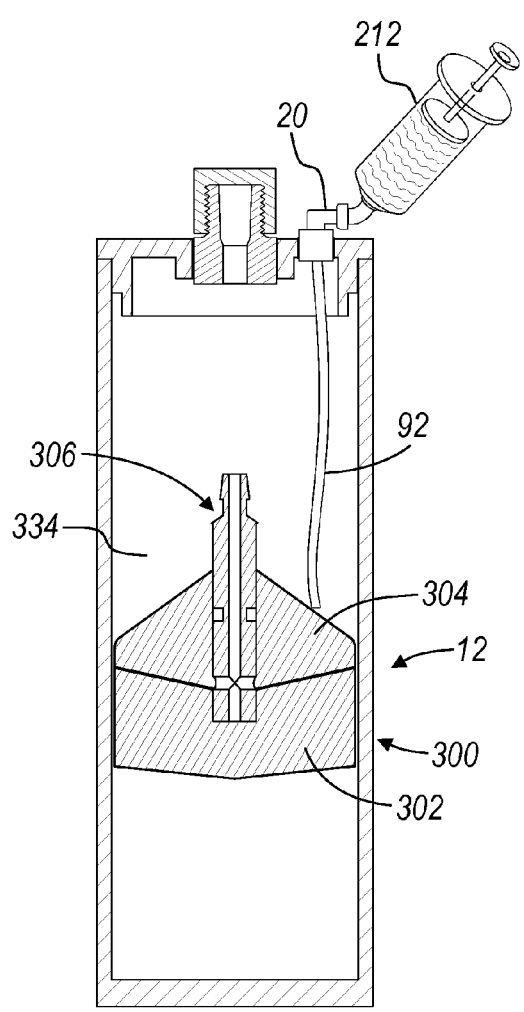
FIG. 7D is a plan view of a second fraction being extracted from the separator according to various embodiments.

With reference to FIG. 7D, once the second fraction 332 has been extracted from the tube 12, the second buoy member 304 may substantially mate with a portion of the first buoy member 302. As discussed above, the second buoy member 304 may substantially only mate with the first buoy member 302 if the second buoy member 304 is able to substantially move relative to the first buoy member 302. Therefore, it will be understood that the second buoy member 304 need not necessarily mate with the first buoy member 302 and is merely exemplary of an operation of various embodiments. Nevertheless, once the second fraction 332 has been extracted from the tube 12, the port 20 may be used in conjunction with a selected instrument, such as a plasma extraction syringe 212 to remove the plasma or the third fraction 334 from the tube 12 using the extraction tube 92 interconnected with the port 20.

As described above, the tube 92 allows for extraction of the third fraction 334 from the tube 12 without comingling the third fraction 334 with the remaining first fraction 330 in the tube 12. Therefore, similar to the separator and extraction system 10, three fractions may be substantially formed within the tube 12 with the buoy system 300 and may be extracted without substantially comingling the various fractions. Once the third fraction 334 is extracted from the tube 12, the buoy system 300 may be removed from the tube 12, such that the first fraction 330 may be removed from the tube 12. Alternatively, the first fraction 330 may be discarded with the tube 12 and the buoy system 300 as a disposable system. Alternatively, the system may be substantially reusable, such that it can be sterilized and may be sterilized for various uses.

The description of the method of use of the buoy system 300 is exemplary of a method of using a system according to various other embodiments. It will be understood, however, that various specifics may be used from various embodiments to allow for the extraction of selected fractions. For example, the centrifugation process may be substantially a single step centrifugation process. The buoy system 300, according to various embodiments, may allow for the formation of three fractions during a single centrifugation process. This centrifugation process may occur at any appropriate speed, such as about 1000 rpms to about 8000 rpms. This speed may produce a selected gravity that may be approximately 4500 times greater than the normal force of gravity. Nevertheless, these specifics are not necessary to the operation of the buoy system 300 according to various embodiments. The buoy system 300, according to various embodiments, may be used to extract a plurality of fractions of a sample after only a single centrifuging process and without substantially comingling the various fractions of the sample.

Figure 8:
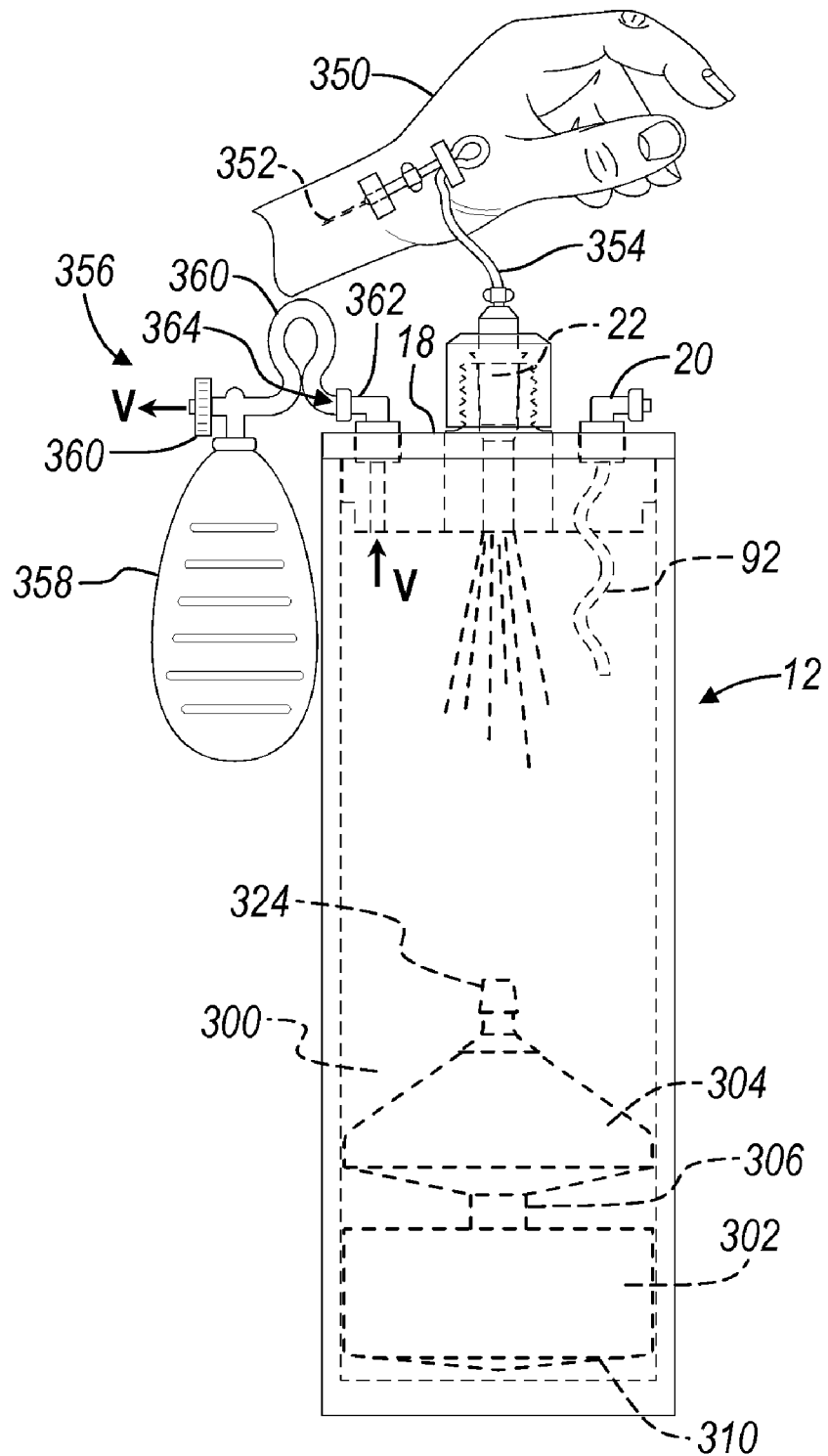
FIG. 8 is a schematic view of an assisted blood withdrawal device.

With reference to FIG. 8, the blood collection and separation system that includes the tube 12, according to various embodiments, may be filled with a multi-component fluid or solution, such as blood from a patient, is illustrated. The tube 12 may include any appropriate separation system, such as the separation system 300. Nevertheless, in addition to filling the tube 12 with a fluid from the syringe 204 any appropriate method may be used to fill the tube 12. For example, when a solution, including a plurality of components, is placed into the tube 12 it may be collected directly from a source.

For example, a patient 350 may be provided. The patient 350 may be provided for a selected procedure, such as generally an operative procedure or other procedure that requires an intravenous connection 352, such as a butterfly needle, to be provided in the patient 350. The intravenous connection 352 generally provides a tube 354 extending therefrom. The tube 354 may be used to withdraw fluids from the patient 350 or provide materials to the patient 350, such as medicines or other selected components. Nevertheless, the intravenous connection 352 is generally provided for various procedures and may be used to fill the tube 12.

The tube 354 may interconnect with the plunger port 22 or any appropriate portion of the tube 12. The port 22 may be used to connect with the tube 354 in a similar manner as it would connect with the syringe 204, if the syringe 204 was provided. Nevertheless, it will be understood that the tube 354 may be provided directly to the tube 12 from the patient 350. This may reduce the number of steps required to fill the tube 12 and reduce possible cross-contamination from the patient 350 with the various components. Moreover, making a connection directly with the patient 350 may make the withdrawal and collection of blood from the patient 350 more efficient.

Once the tube 354 is interconnected with the tube 12 the pressure differential between the patient 350, such as the intravenous pressure of the blood, may be used to fill the tube 12 to a selected volume. In addition, a vacuum system 356 may be provided The vacuum system 356 may include a vacuum inducing portion or member 358, such as a resilient bulb. The vacuum inducing member 358 may be interconnected with the tube 12 through a selected connecting portion 360.

The vacuum connecting portion 360 may interconnect with an orifice 362. The orifice 362 may be interconnected or extend from the cap 18 or provided in any appropriate portion with the tube 12. Nevertheless, a first one way valve 364 may be provided along the connection portion 360 or near the orifice 362. The one way valve 364 provides that a flow of a fluid, such as a gas, may pass in a first direction but not in a second. A second one way valve 366 may also be provided downstream from the first one way valve 364. In this way, a vacuum may be created with the vacuum inducing member 358, such that air is drawn out of the tube 12 and removed through the second one way valve 366 in the direction of arrow V. Due to the first and second one-way valves 364, 366 the air is generally withdrawn from the tube 12 without substantially allowing the air to flow back into the tube 12. Thus, a vacuum can be created within the tube 12 to assist with removing a selected volume of fluid, such as blood, from the patient 350.

Because the tube 12 may be filled substantially directly from the patient 350, the collection of the fluid, such as blood, may be provided substantially efficiently to the tube 12. Although any appropriate mechanism may be used to assist in withdrawing the blood from the patient 350 the vacuum system 356 may be provided including the vacuum inducing member 358. Any appropriate vacuum creating device may be used, such as a mechanical pump or the like. Nevertheless, the tube 12 may be filled for use during a selected procedure.

As discussed above, the tube 12 may be used to separate a selected portion of the blood obtained from the patient 350 substantially intraoperatively. Therefore, the collection or separation of the various components may be substantially autologous and substantially intraoperatively. Moreover, obtaining the fluid directly from the patient 350 may increase the efficiency of the procedure and the efficiency of the intraoperative or the operative procedure.

Figure 9:
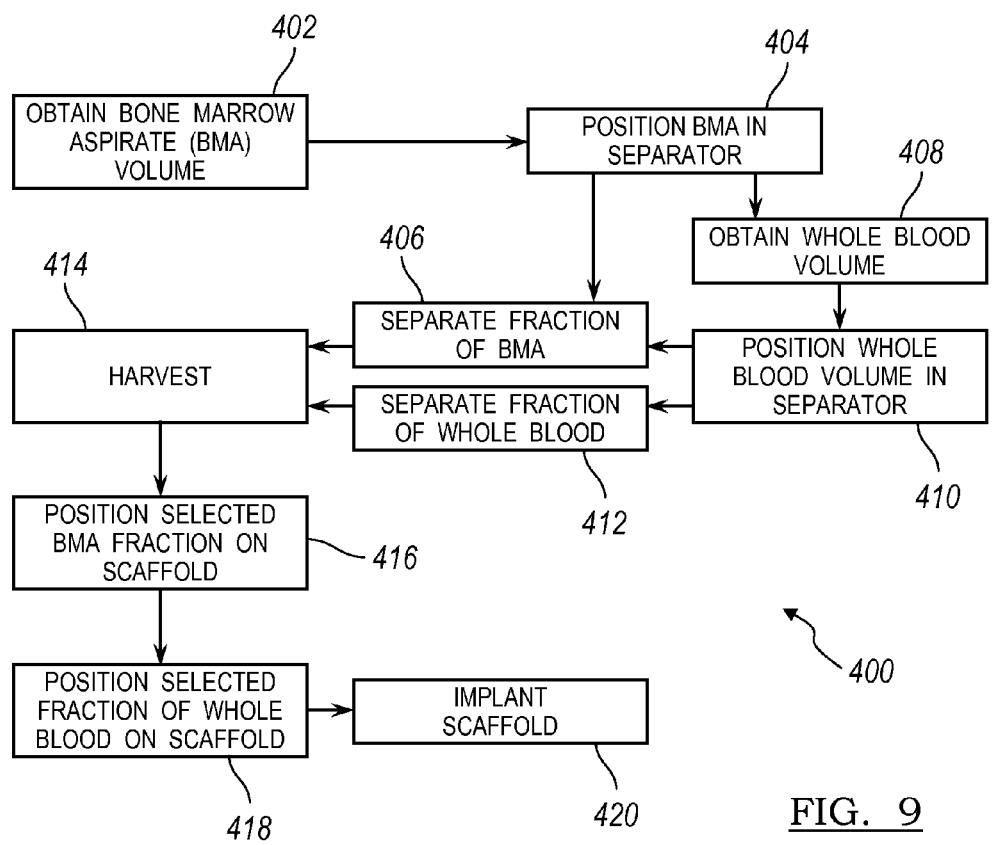
FIG. 9 is a block diagram of a method for implanting selected fractions of a fluid.

With reference to FIG. 9, the separator 10 may be used to separate any appropriate material. The material may be separated for any purpose, such as a surgical procedure. For example, a selected fraction of a bone marrow aspirate or a bone marrow portion may be produced with the separator 10 according to various embodiments. The selected fraction of the bone marrow aspirate may include various components, such as undifferentiated cells. The various undifferentiated cells may be positioned in a selected scaffold or relative to a selected portion of a patient for providing a volume of the undifferentiated cells to the patient. It will be understood that the method described according to FIG. 9 is merely exemplary of various embodiments that may be used to provide a selected fraction of a bone marrow aspirate or other material to a patient or selected position. The selected portion may be placed on the scaffold in any appropriate manner, such as by spraying, dipping, infiltrating, or any appropriate method.

A method of selecting or creating a selected fraction of a bone marrow aspirate in a selected scaffold according to a method 400 is illustrated in FIG. 9. Generally, the method 400 may start in block 402 in obtaining a bone marrow aspirate volume. The bone marrow aspirate (BMA) may be obtained in any selected or generally known manner. For example, a selected region of bone, such as a portion near an operative procedure, may be used to obtain the bone marrow aspirate. Generally, an accessing device, such as a syringe and needle, may be used to access an intramedullary area of a selected bone. The BMA may then be withdrawn into the syringe for various procedures. Once a selected volume of the BMA is obtained in block 402, the BMA may be positioned in the separator 10 according to various embodiments in block 404. The BMA may be positioned in any appropriate separator, such as those described above including the separator 10. Once the BMA is positioned in the separator 10, a selected fraction of the BMA may be separated from the BMA in block 406.

The selected fraction of the BMA may include undifferentiated cells or any appropriate portion of the BMA. The fractionation or separation of various fractions of the BMA may allow for a volume of BMA to be taken from a single location and the separation or concentration of the selected portion may be performed in the separator 10. Generally, obtaining a small volume of the selected portion from a plurality of locations may be used to obtain an appropriate volume of BMA or selected fraction of the BMA. Nevertheless, the separator 10 may allow for separating a selected volume from a single location from which the BMA is obtained. This may reduce the time of a procedure and increase the efficiency of obtaining the selected fraction of the BMA.

In addition to obtaining a volume of the BMA in block 402, a volume of whole blood may be obtained in block 408. The volume of blood obtained in block 408, according to any appropriate procedure, including those described above, may then be positioned in the separator 10, in block 410. The whole blood may be positioned in any appropriate separator, such as those described above or a separator to separate a selected fraction of the whole blood. As described above, the whole blood may be separated into an appropriate fraction, such as a fraction including a platelet portion or buffy coat. The whole blood may be separated into selected fractions in block 412. It will be understood that the BMA and the whole blood volume may be obtained substantially simultaneously or consecutively in block 402 and 408. Similarly, the selected fractions of the BMA obtained in block 406 and whole blood obtained in block 412 may also be performed substantially sequentially or simultaneously. For example, the separator 10 including the volume of the BMA may be positioned in a separating device, such as a centrifuge, substantially opposite, so as to balance, the separator 10 including the volume of the whole blood. Therefore, a single separation, such as centrifuge procedure may be used to separate both the BMA and the whole blood into selected fractions. This again may increase the efficiency of the procedure to provide both a selected fraction of the BMA and a selected fraction of the whole blood substantially simultaneously.

The selected fractions of the BMA and the whole blood, provided in block 406 and 412 may be harvested in block 414. The selected fractions of the BMA and the whole blood, may be harvested in block 414 for appropriate purposes, such as those described herein. The separator 10 may be used to obtain the selected fractions of the BMA and the whole blood, through various procedures, such as those described above.

After harvesting the selected fractions of the BMA and the whole blood in block 414, the selected fraction of the BMA may be positioned on an appropriate scaffold in block 416. The scaffold in block 416 may be any appropriate scaffold, such as synthetic bone substitutes or allogenic tissue. The scaffolds may be used for appropriate procedures, such as hard or soft tissue grafting, including uses in non-union or chronic wounds. The undifferentiated cells of the BMA may allow for a substantial source of cells for use during a substantially natural healing after an operative procedure, for example, the natural healing of a patient may use the supplied undifferentiated cells. Therefore, the scaffold may be positioned in a selected portion of the anatomy and the cells may be allowed to grow and differentiate into selected portions in the implanted position.

In addition to positioning the selected fraction of the BMA and the scaffold in block 416, the platelets of the whole blood may be positioned on or near the scaffold of block 418. The platelets of the whole blood fraction positioned in the scaffold of block 418 may assist the undifferentiated cells and the anatomy into which the scaffold is positioned to allow for a substantially efficient and complete healing. The platelet fraction of the whole blood sample may include various healing and growth factors that may assist in providing an efficient and proper healing in the anatomy. Therefore, the undifferentiated cells of the BMA, or other selected fraction obtained from the separation of the BMA, and the selected fraction of the whole blood, obtained from the separator, may be used with the scaffold to provide a substantially efficient implant. In addition, the separator 10, or any appropriate separator, such as that described above, may allow for a substantially quick and efficient separation of the BMA and the whole blood into an appropriate fraction for use in the procedure.

After the selected portion of the BMA and the whole blood are positioned on the scaffold in blocks 416 and 418 the scaffold may be implanted in block 420. As described above, the scaffold may be implanted in any appropriate position in the block 420 for various procedures. It will be understood that the scaffold may be implanted for any appropriate procedure and may allow for positioning the selected portion of the BMA, such as undifferentiated cells, and the selected portion of the whole blood, such as platelets, relative to a selected portion of the anatomy. The scaffold may allow for a bone ingrowth, such as allowed with the undifferentiated cells, to assist in healing of a selected portion of the anatomy.

Figure 10A:
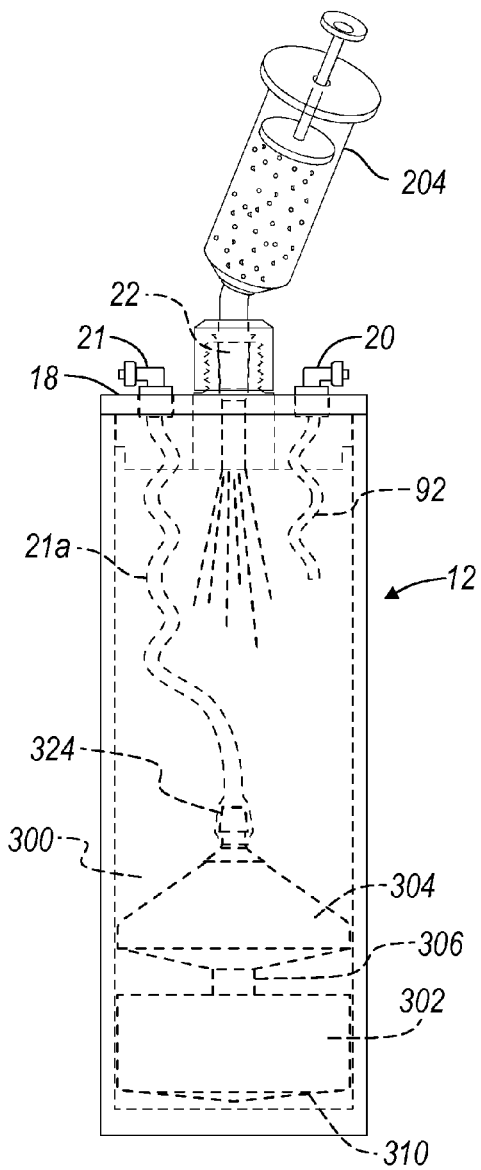
FIGS. 10A-10C is a plan view of a separator system in operation.
Figure 10B:
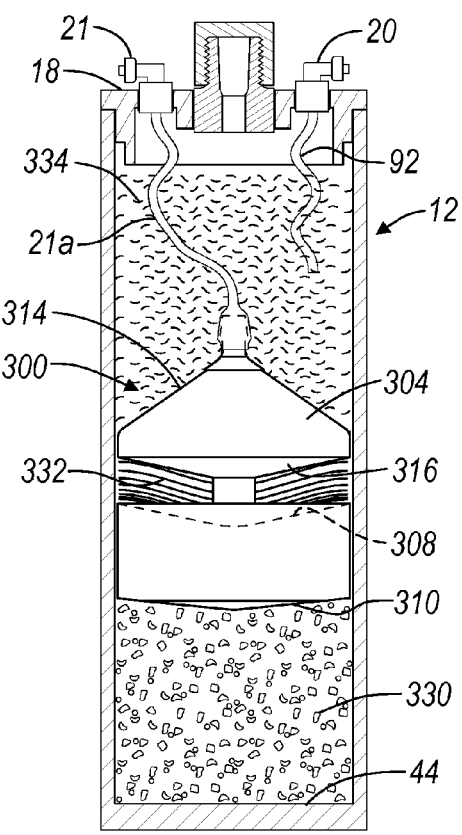
Figure 10C:
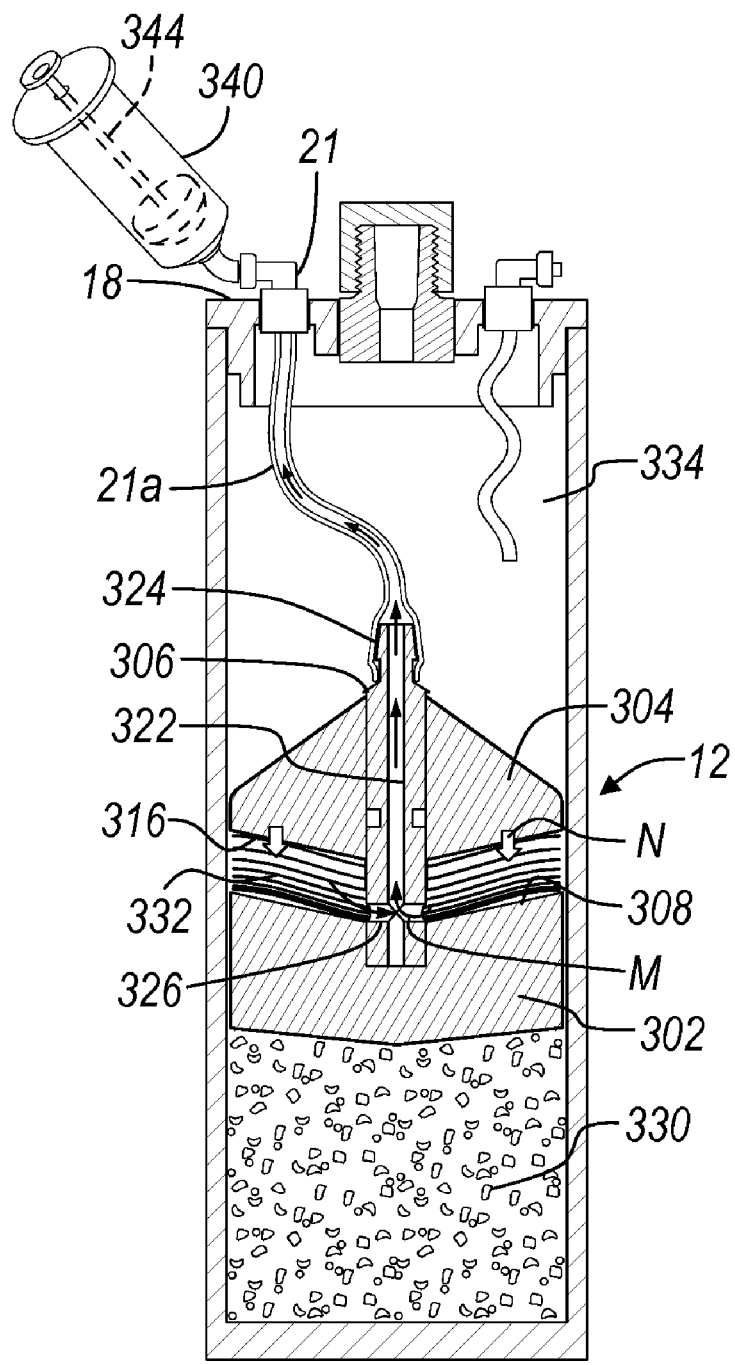

With reference to FIGS. 10A-10C the separator 10 can include alternative or multiple portions, apparatuses, or systems to assist in removing any selected portion or fraction from the tube 12. For example, the tube 12 can also include a second port 21, which may also be referred to as a plasma rich port (PRP). A second flexible member, such as a flexible tube 21a, can interconnect the PRP port 21 and the connection portion 324 of the buoy cylinder 306.

The syringe 204 can be used to introduce a whole sample, such as whole blood, BMA, combinations thereof, or any appropriate material, to the tube 12, as discussed above. The tube 12 can then be placed in a centrifuge, or similar device, to separate the whole material into selected fractions. As the buoy system 300 moves, as discussed above, the flexible tube 21a can remain attached to the cylinder 306. As discussed above, as the centrifuge forces decrease the tube 12 will decompress and assist in holding the buoy system 300 in place, as illustrated in FIG. 10B.

Once the centrifugation is complete the extraction syringe 340 may be interconnected with the PRP 21 that is interconnected with the connection portion 324 of the buoy cylinder 306 via the flexible member 21a. As discussed herein the buoy cylinder allows access to the platelet rich area 332 between the buoy portions 302,304. Thus, it will be understood, that access may be obtained and the platelet rich portion of the sample 332, between the two buoys 302,304, may be extracted in a plurality of ways. The illustrations and method described herein are merely exemplary.

Figure 11:
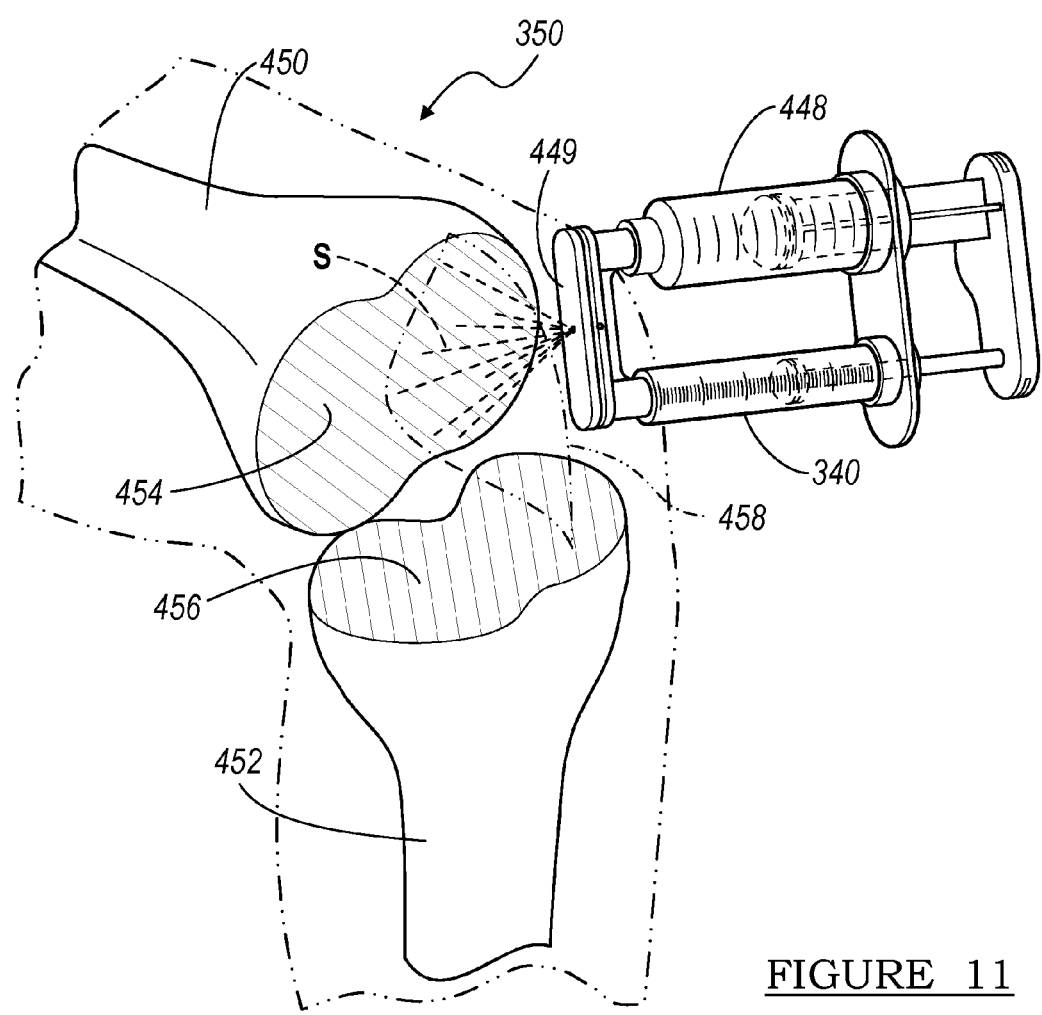
FIG. 11 is an environmental view of a sprayer system with a two-part mixture being expressed onto a portion of an anatomy.

Also, the various fractions of the material can be used for various purposes, including those discussed above and herein. The various fractions that can be created with a separator 10 can be applied to various portions of the patient 350 for selected purposes. For example, the various fractions or components, for example of whole blood, can include various growth factors, anti-infection or anti-microbial components, and other selected portions. These materials can be applied to the patient 350 (FIG. 11) for various purposes such as infection prevention or reduction, speed healing, speed in growth, and the like.

As discussed above, the platelet rich plasma and the platelet poor plasma can be withdrawn from the separator 10 according to various embodiments. For example, the extraction syringe 340 can be used to extract the platelet rich plasma 332 from the tube 12. It will be understood that the platelet rich plasma can be formed in any appropriate manner, including according to various embodiments discussed above.

If the platelet rich plasma is withdrawn into the extraction syringe 340, the extraction syringe can be used to apply a selected material, such as the platelet rich plasma fraction 332 onto the patient 350.

It will be understood that the platelet rich plasma and the extraction syringe 340 can be mixed with any selected component either during the application, prior to application, or at any appropriate time. For example, the extraction syringe 340 can be interconnected with an application syringe 448 as part of an application system 449. The application system can be any appropriate application system such as the one provided with the GPSII system sold by Biomet, Inc. It will be understood, however, that the application system 449 can be any appropriate application system.

The application system 449, can form a mixed spray S that can be sprayed onto a selected portion of the patient 350. For example, during a procedure, such as during a total, partial, or the like knee replacement, a femur 450 and a tibia 452 may be resected for various purposes. The resected portion of the femur 454 and the resected portion of the tibia 456 may have a portion of the mixture, or any appropriate fraction, sprayed thereon for various purposes. For example, the various portions of the whole blood fraction can include growth factors that assist in bony re-growth or healing after the application of the material. The implant portions can then be positioned relative to the femur 450 and the tibia 452 and healing can occur thereafter.

Further, an incision 458 can be formed through the soft tissue of the patient 350 to gain access to the various portions, such as the femur 450 and the tibia 452. A portion of the material, such as a mixture of the platelet rich plasma from the extraction syringe 340 can be mixed with a select other components, such as a material positioned in the second syringe application syringe 448 and sprayed onto soft tissue surrounding the incision 458. The mixture can be any appropriate mixture, a thrombin can be included in this second application syringe 448 and mixed with platelet rich plasma in the extraction syringe 340. Alternatively, or in addition thereto, various other clotting agents, pharmaceuticals (e.g., antibiotics, medicines and the like) can be included in the second application syringe 448. Further, any of the selected materials can be mixed with the platelet rich plasma in the extraction syringe 340 and applied to the patient 350 and in any appropriate manner.

It will be understood that the various fractions, such as the platelet poor plasma, the platelet rich plasma, the buffy coat, and the like, can be applied to the patient 350 and can be formed with the separator 10 according to various embodiments. In addition to the various pharmaceuticals, the buffy coat can provide a selected amount of white blood cells to the wound 458, the resected site 454, 456, and the like to assist in reducing or inhibiting post-operative infection and can assist with healing after an operative procedure. Nevertheless, the various components can be formed autologously from the patient's whole blood, from their Bone Marrow Aspirate (BMA), or other biological fluids or materials. Therefore, as discussed above, the chance of contamination because of the use of an external source is reduced.

It will be understood that the selected fraction of the component can be applied during any appropriate procedure for purposes such as speed in healing, anti-infection action or the like. For example, the buffy coat, including the selected portion of white blood cells, platelet anti-microbial peptides and the like can be applied during a cesarean section operation, orthopedic operation, cosmetic operative procedures or the like. It will be understood that the various examples are not intended to limit the teachings or applications of the selected materials such as buffy coat, which can be formed with the separator 10. Further, the additional materials that can be added to the buffy coat fraction, the other fractions, or the like, are also intended to be merely exemplary and not intended to limit the teachings herein.

As discussed above, the various portions or fractions can be used for assisting in healing, regrowth, and infection or the like. As discussed above the fraction, such as the buffy coat, can include high concentrations of white blood cells or other selected blood components. These fractions, such as the white blood cells can assist in anti-infection and healing of a patient or anatomy. For example, the material can assist in reducing infection after an incision is made and during healing.

Also, as discussed above, the selected fraction can be mixed with other materials for application to a patient. For example, the buffy coat can be mixed with other anti-infection materials, such as pharmaceuticals (i.e. antibiotics) to be applied to a surgical site. Nevertheless, as discussed above the materials can be applied to a surgical site, such as a soft tissue incision, a resected bone portion, or the like for various purposes, such as anti-infection, help in healing, or the like.

Various biological materials or factions thereof can be formed according to selected methods and using various apparatuses. Apparatuses according to various embodiments, including those discussed herein, can be used to separate a selected fraction of a whole material for various purposes. According to the various embodiments discussed above, a buoy or buoy system, that can also be referred to as separation system, can be used to assist in separating a whole material into various and/or plurality of fractions. It will be understood, however, that any appropriate separation system can be provided to assist in separating a material.

Figure 12:
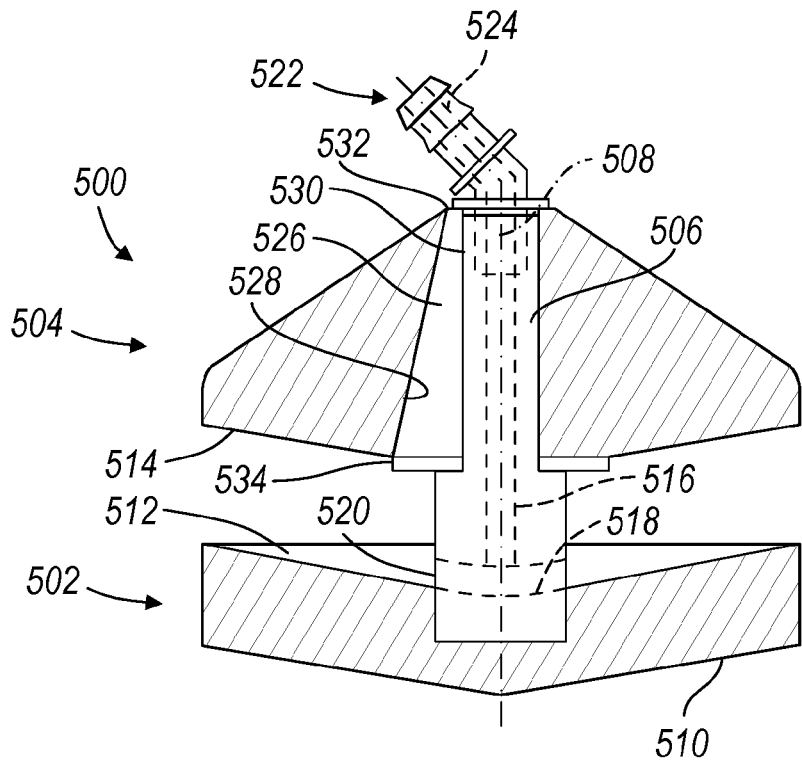
FIG. 12 is a partial cross-section view of a bouy system according to various embodiments.

For example, with reference to FIG. 12, a buoy or separation system 500 is illustrated. The buoy system 500 can include portions that are similar to portions discussed above, such as the buoy system 300. As discussed above, the buoy system 300 includes a first buoy portion 302 and a second buoy portion 304. The first buoy portion 302 can move relative to the second buoy portion 304 along the connection portion 306. The second buoy portion 304 can seal relative to a portion of the connection portion 306, such as an O-ring or other appropriate sealing interaction, including a tight fit between the second buoy member 304 and the connection member 306.

The buoy system 500, however, can also include a first buoy portion 502 and a second buoy portion 504. The buoy portions 502, 504 can be formed substantially fixed relative to one another with a connection member 506. The connection member 506 can extend along an axis 508 that can be similar to the axis D discussed above. The connection member 506, however, can fixedly interconnect to the first buoy member 502 and the second buoy member 504. During use of the buoy system 500, the buoy portions 502, 504 remain substantially fixed relative to one another such that they are not able to move relative to one another.

Nevertheless, the second buoy member 502 can define a bottom surface 510 that includes features similar to the bottom surface 310. Further, the first buoy portion 502 can also define a collection face 512 that can include features similar to the collection face 308. The second buoy portion 304 can also define a bottom surface 514 that can include any appropriate configuration, such as the bottom surface 316. Nevertheless, the bottom surface 514 of the second buoy portion 504 need not be formed to substantially mate with the collection surface 512 of the first buoy member 502 as the buoy portions are substantially fixed relative to one another.

Further, the buoy system 500 can be formed in various ways. For example, the buoy system can be formed as a single member, formed of a single piece, or can be formed of multiple pieces that are interconnected to form the buoy system 500. Nevertheless, the buoy system 500 can include any selected density or specific gravity, including those discussed above. It can be selected to form the buoy system 500 to include a density that can substantially position the collection face 512 generally below a fraction including the buffy coat of the whole blood sample. It will be understood that such a density can be any appropriate density such as about 1.00 gram per cc to about 1.10 grams per cc. Nevertheless, the entire buoy system 500 can be designed or formed to include the selected density because the portions of the buoy do not move relative to one another. It will be understood, however, that any appropriate portion of the buoy system 500 can be a formed to include the selected density.

The connection member 506 defines a central or first bore 516 passing through the connection portion 506. The central bore 516 can interconnect with a second or traversing bore 518 that includes an opening or multiple openings 520 near the collection surface 512. This can allow a material that is collected near the collection surface 512 to be transported through the central bore 516 as discussed above and further herein. Further, a hose connection 522 can be provided that defines a bore 524 that interconnects with the central bore 516 of the connection member 506. Although the various portions, including the connection member 506 and the tube connection 522 can be formed as a single member with the other portions of the buoy system 500 or can be formed of separate portions that are interconnected.

The second buoy member 504 can be fixedly connected to the connection portion 506 in any appropriate manner. For example, the second buoy portion 504 can be formed as a single member or a single piece with the connection member 506. Further, the second buoy portion 504 can be connected to the connection member 506 using any appropriate method such as welding, adhesives, or any appropriate method. Nevertheless, a gap or passageway 526 can be defined between an inner wall 528 of the second buoy portion 504 in an outer surface 530 of the connection member 506.

The passage 526 can be provided in any appropriate number in or through the second buoy member 504. The passage 526 can be opened at a selected end such as a top end 532 of the second buoy member 504. As discussed herein, this can allow selected materials to pass through the passage 526 at a selected time. A sealing member or check valve 534 can be provided at a second end of the channel 526 such as an area between the bottom surface 514 of the second buoy member 504 and the collection surface 512. The check valve 534 can allow for passage of a selected material upon the application of a force, such as centrifuging, a vacuum, or the like. The check valve 534 can be any appropriate portion, such as a substantially flexible washer or member that is positioned relative to the second buoy portion 504. The check valve 534 can include a washer or flat portion that is formed of any appropriate material such as a silicone material, a rigid material including a living hinge, or any appropriate configuration. Nevertheless, the check valve 534 can allow for a selected passage of a material or an inhibition of a passage of material at a selected time.

Figure 13:
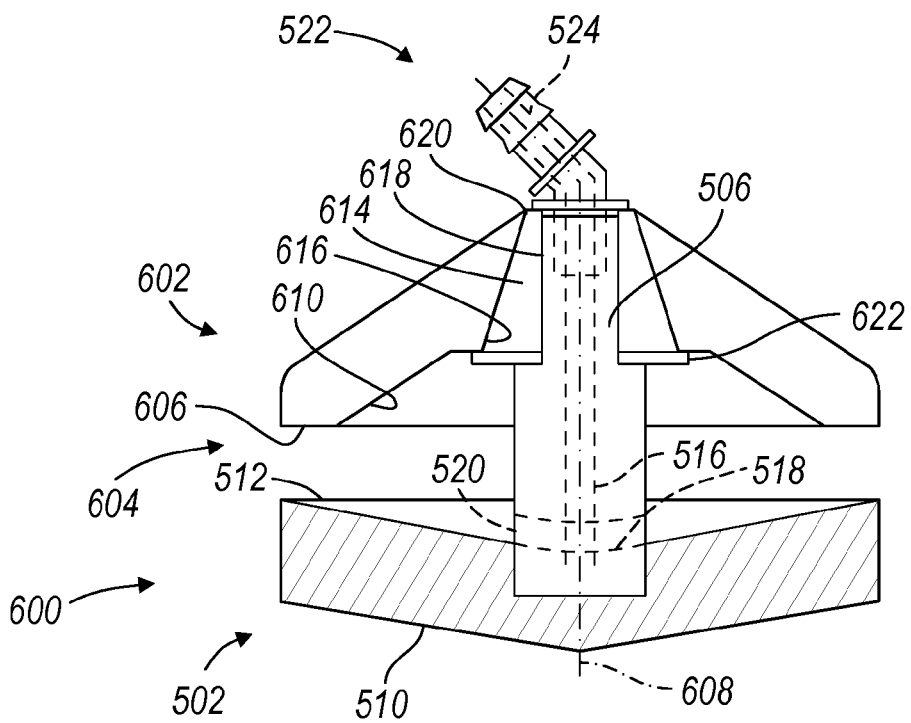
FIG. 13 is a detail partial cross-section view of a bouy system according to various embodiments.

With reference to FIG. 13, a buoy system 600, according to various embodiments, can be provided that is similar to the buoy system 500 illustrated in FIG. 12. The buoy system 600 can include portions that are similar to the portions of the buoy system 500 and like reference numerals are used to reference these portions for brevity of the current discussion. For example, the buoy system 600 can include a bottom buoy portion 502, a collection surface 512, a connection member 506, and bores 516 and 518 that pass through the connection portion 506. As discussed above, the bore 518 can terminate or include a passage or opening 520 that can allow access to the internal bores from the collection surface 512. Further, a hose connection 522 can be provided to interconnect with the selected tool and a bore 524 can be provided therein.

The buoy system 600 can also include a second buoy portion 602 that is similar in operation but different in design from the second buoy portion 504. The second buoy portion 602 can include a top surface that includes a geometry and design substantially similar to the second buoy portion 504. A bottom surface 604, however, of the second buoy member 602 can include a first surface portion of 606 that can be substantially flat or perpendicular to a central axis of 608 of the buoy system 600. A second surface portion 610 can also be defined by the second buoy portion 602 that substantially increases a volume between the collection surface 512 and the bottom surface 604 of the second buoy member 602 relative to the second buoy member 504 illustrated in the buoy system 500. It will be understood that the various surfaces 606, 610 can be provided for any appropriate reason, such as providing a selected volume, separating a selected volume, or any appropriate purpose. Nevertheless, it will be understood that the various portions of the buoy systems according to various embodiments can be configured and designed for any appropriate purpose, such as separating a selected volume of material, achieving or sequestering a selected volume of material, or any other appropriate purpose.

The first buoy portion 502, second buoy portion 602, the connecting portion 506, and the tube connection 522 can be fixed together in any appropriate manner. For example, the various portions can be formed from a single piece such that they are formed as a single member or piece such as with injection molding, machining, or the like. Further, various portions can be interconnected in any appropriate manner, such as welding, adhesives, or the like. Nevertheless, the second buoy portion 602 can include a passage 614 that is similar to the passage 526 of the buoy system 500.

The passage 614 can be formed and defined between an inner wall 616 of the second buoy member and an outer wall or portion 618 of the connection member 506. The passage 614 can be open at a top end 620 of the second buoy member 602 and can be closed with a check valve 622 near a bottom end of the passage 614. The check valve 622 can be similar to the check valve 534 of the buoy system 500 and can be formed of any appropriate material, configuration or the like.

The buoy systems 500, 600 having been described above include various portions. Although the buoy systems 500, 600 can be formed of differing materials, designs, or the like, they can be provided in the separator 10 to separate, sequester, and provide a selected material.

Figure 14C:
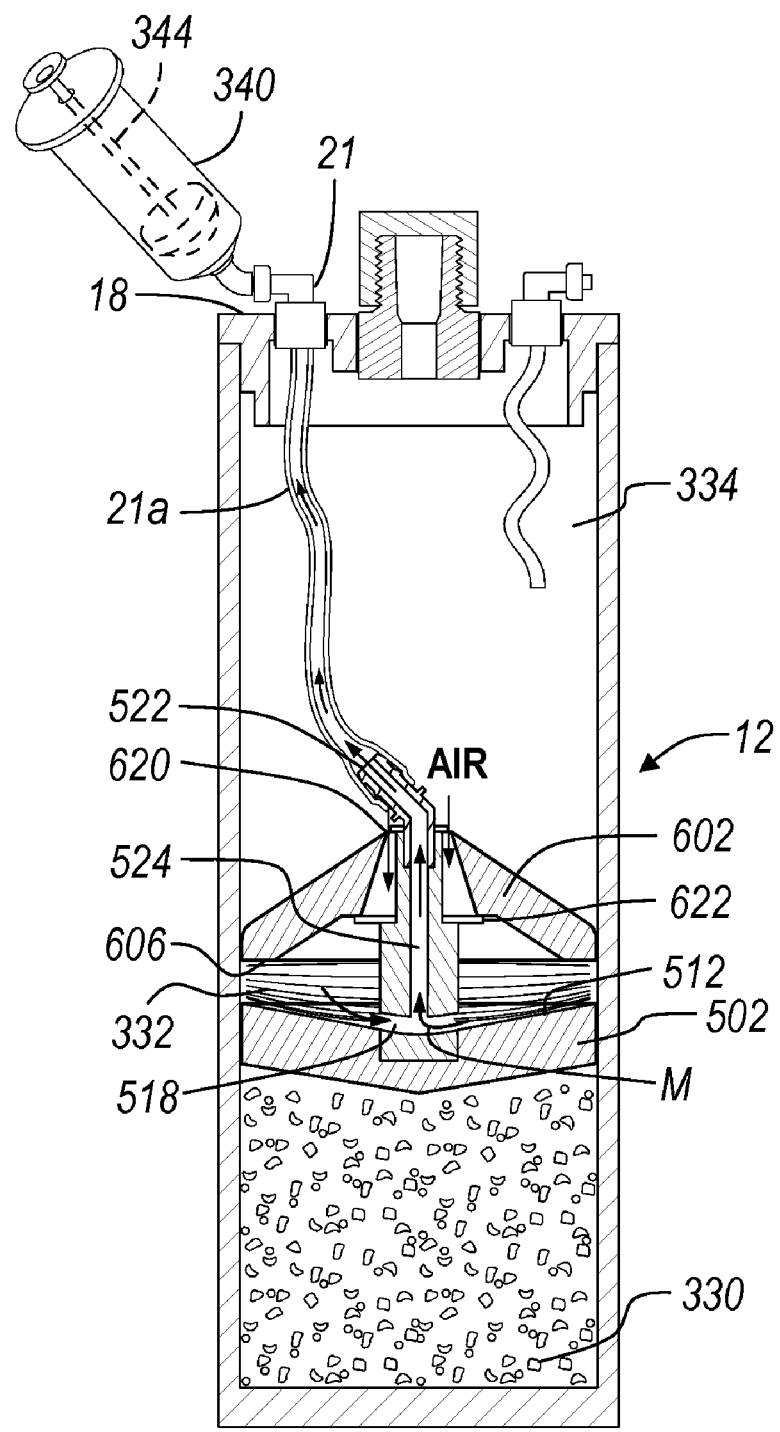

With reference to FIGS. 14A-14C, the buoy system 600 will be described during use for illustration purposes only. It will be understood that the use of the buoy system 600 can be substantially similar to the use of the buoy system 500 and the geometry of the various portions can be selected for various reasons.

With initial reference to FIG. 14A, the buoy system 600 can be provided in the tube 12 as discussed above. The buoy system 600 can be interconnected with a platelet rich plasma port 21 through the tube 21a that interconnects with the tube connection 522. As discussed above, the connection 522 can interconnect with the bores 516 and 518 to obtain access to the collection face 512. Nevertheless, a selected material, such as a whole blood sample from the syringe 200, can be positioned within the tube 12. As discussed above, once the material is positioned within the tube, the separator system 10, including the tube 12 and the buoy system 600, can be positioned in the centrifuge for any selected period of time and under selected conditions, including those discussed above. During the centrifugation of the separator system 10, the walls of the tube 12 may flex, the buoy system 600 may move, and any other appropriate condition may occur, including those discussed above. Nevertheless, the buoy system 600 includes a selected density, specific gravity or other appropriate configuration can move to a selected region within the whole sample positioned within the tube 12.

As discussed above, a buffy coat fraction or area 332, that may also be referred to as a platelet rich plasma (PRP), can be substantially defined between an area of the second buoy portion 602 and the first buoy portion 502. In a region above the second buoy portion 602 near the cap 18, may be a platelet poor plasma (PPP) or area 334, as discussed above. The PPP tube 92 can interconnect with the PPP port 20 for access to the PPP fraction 334.

As discussed above, the buoy system 600 can define a passage 614 or any appropriate number of passages. During the centrifugation process, a portion of the material, such as the PRP 332, the PPP 334, or any other appropriate material may pass through the passage 614 because of the check valve 622. Therefore, the passage 614 can be provided to allow for ease of separation and movement of the buoy system 600 for various reasons.

After the centrifugation, the buoy system 600 can come to rest at a selected region within the tube 12, as illustrated exemplary in FIG. 14B. A syringe or other appropriate device can be interconnected with the PPP port 20 such that the PPP 334 is substantially withdrawn from the tube 12. It will be understood that the withdrawal tube 92 can extend to substantially near the second buoy portion 602 to allow for a substantially complete withdrawal of the PPP 334.

As illustrated in FIG. 14C, once the PPP 334 is substantially removed from the tube 12, the upper portion of the tube 12 can be filled with an empty space or atmospheric air. Therefore, the two remaining fractions, including various platelet materials 330 and the PRP or a selected middle fraction 332 is left between the buoy portion 602, 604. Briefly, it will be understood that the separation system 10 can be used to separate any appropriate material in the separation of a whole blood sample or materials including blood is merely exemplary. Nevertheless, the PRP 332 can be accessed through the PRP tube 21a that is interconnected with the PRP port 21.

A withdrawal device or extraction device, such as the syringe 340, can be interconnected with the PRP port 21. A vacuum can be formed in the syringe 340 with the plunger 344 such that a vacuum is also formed within the bores 516, 518 of the connection member 506. With the vacuum, the PRP 332 can be withdrawn through the opening 520, the bores 516, 518, and the bore 524 through the tube connection 522 and into the syringe 340. As the material is drawn from the collection face 512, the check valve 622 can move to allow atmospheric air to enter into the area defined between the surfaces 604, 610 and the collection face 512. Because of the check valve 622, the pressure differential between the area of the collection phase 512 and the atmospheric pressure surrounding tube 12 and other portions can be substantially released as the material is drawn within to the syringe 340. Therefore, the material can be easily drawn into the syringe 340, substantially all the material can be drawn into the syringe 340, and a back pressure is released to maintain the PRP in the syringe 340.

It will be understood that the buoy systems 500, 600 can be used with any appropriate system. The separator 10, according to various embodiments, including those discussed herein, can be provided for various purposes, such as those discussed above. The buoy systems 500, 600 can be used in the separator 10 as can any of the other appropriate buoy or separation systems. The separation buoy systems 500, 600 are merely exemplary and not intended to limit the teachings included herein. It will be understood that separator 10 can be used including any appropriate portions to achieve a separation, sequestering, extraction, or the like of any appropriate materials that are positioned within the separator 10. The discussion of the use of any selected buoy system, also referred to as a separation system, or the like, is merely exemplary and intended to provide various illustrative devices or applications. Nevertheless, the buoy systems 500, 600 can be provided to achieve selected results in a separation system 10.

The description of the teachings is merely exemplary in nature and, thus, variations that do not depart from the gist of the teachings are intended to be within the scope of the teachings. Such variations are not to be regarded as a departure from the spirit and scope of the teachings.

What is claimed is:
1. A system for separating and extracting selected fractions from a container, the system comprising:
 a container to contain the whole material; and
 a separation system operable to be positioned within the container, including:
  a first separation member;
  a second separation member;

a third separation member operably interconnecting said first separation member and said second separation member; and a check valve positioned relative to the second separation member that allows for movement of a material past said second separation member through a checked passage defined between said third separation member and said second separation member;

wherein each of said first member, said second member, and said third member of the separation system is at least partially fixed at a position relative to each other of said first member, said second member, and said third member of the separation system; and wherein said third separation member allows access to a volume defined between said first separation member and said second separation member.

2. The separation system of claim 1, wherein the separation system includes a density of about 1.00 g/cc to about 1.10 g/cc.

3. The separation system of claim 1, wherein said second separation member includes a lower surface defining an apex;

wherein the portion of said second separation member that engages a bottom of said container is substantially limited to said apex.

4. The separation system of claim 1, further comprising a pressure system operable to form a pressure differential in said container different from a pressure external to said container.

5. The separation system of claim 4, further comprising an intravenous conduit operable to be connected with an intravenous portion of a patient and directly to said container such that the pressure formed in said container is different from a pressure in the intravenous system operable to form a flow of material into said container.

6. The separation system of claim 1, wherein said third separation member defines a passage extending between a volume defined between said first separation member and said second separation member and an end of said third separation member.

7. The separation system of claim 1, further comprising:
an extraction instrument operable to be interconnected with said third separation member to withdraw a selected volume from between said first separation member and said second separation member.

8. The separation system of claim 1, further comprising a port extending from said container;
a flexible tube interconnecting said third separation member and said port;
wherein said extraction instrument operably interconnects with said port to be fluidly connected to a volume between said first separation member and said second separation member;
wherein said flexible tube maintains a connection between said third separation member and said port during a centrifugation of said container with said separation system positioned within said container.

9. The separation system of claim 1, further comprising:
a centrifuge;
wherein said container is disposable in said centrifuge during a centrifugation process to form at least two fractions of a selected sample and said separation system is operable to move to a position within said container during said centrifugation process to at least separate the two fractions.

10. The separation system of claim 1, wherein said separation system is formed from a single member.

11. The separation system of claim 1, wherein said first separation member, said second separation member and said third separation member are formed as separate pieces that are fixably interconnected.

12. The separation system of claim 11, wherein the fixed interconnection of the first separation member, the second separation member, and the third separation member includes adhesives, welding, injection molding, mechanical fixation and the like.

13. The separation system of claim 1, wherein said check valve includes a flexible washer, a member including a living hinge, a spring, or combinations thereof.

14. The separation system of claim 1, wherein said check valve is operable to move during extraction of a volume with said extraction instrument.

15. The separation system of claim 1, wherein said second separation member defines a passage therethrough and said check valve is operable to close at least a portion of the passage defined by said second separation member.

16. A system for separating and extracting selected fractions from a container, the system comprising:
a container to contain the whole material; and
a separation system positioned within said container, including:
a first separation member;
a second separation member;
a third separation member operably interconnecting said first separation member and said second separation member, wherein said third separation member includes a passage extending into at least a portion of a dimension of said third separation member; and
a check valve positioned relative to said third separation member to selectively seal a checked passage formed relative to said first separation member to allow for movement of a material relative to said first separation member;
wherein the first separation member is fixed relative to the second separation member;
wherein said passage of said third separation member allows access to a volume defined between said first separation member and said second separation member:
wherein said check valve allows for passage of a selected material upon the application of a force through said checked passage;
wherein said check valve is operable to open said checked passage upon the application of a vacuum to withdraw a material from between said first separation member said second separation member through said passage in said third separation member.

17. A system for separating and extracting selected fractions from a container, the system comprising:
a container to contain the whole material; and
a separation system positioned within said container, including:
a first separation member;
a second separation member;
a third separation member operably interconnecting said first separation member and said second separation member, wherein said third separation member includes a passage extending at least a portion of a dimension of said third separation member; and
a check valve positioned relative to said third separation member to selectively seal a checked passage formed relative to said first separation member to allow for movement of a material relative to said first separation member;

wherein the first separation member is fixed relative to the second separation member;

wherein said passage of said third separation member allows access to a volume defined between said first separation member and said second separation member:

wherein said check valve allows for passage of a selected material upon the application of a force through said checked passage;

wherein said check valve includes a flexible member having a portion to engage said first separation member to seal said checked passage.

18. The system of claim 17, wherein said flexible member includes at least one of a substantially flexible washer, a silicone material, or a rigid material including a living hinge.

19. The system of claim 18, wherein said second separation member includes a concave collection surface and said first separation member includes a concave collection surface, wherein the first collection surface and the second collection surface are non-complementary;

wherein said checked passage is defined between said first separation member and said third separation member and said flexible member extends from said third separation member to selectively seal said checked passage.

20. A method for separating and extracting selected fractions from a container, comprising:

centrifuging a container with a separation system therein, the separation system having a first separation member, a second separation member, and a third separation member to form a fraction of a whole material between the first separation member and the second separation member;

wherein a check valve selectively seals a checked passage formed between said first separation member and said third separation member and allows movement of at least a portion of the whole material past said first separation member;

wherein said third separation member is interconnecting said first separation member and said second separation member and said first separation member is fixed relative to said second separation member;

wherein access to a volume between said first separation member and said second separation member is allowed through said third separation member.

21. The method of claim 20, further comprising:

withdrawing said fraction from between said first separation member and said second separation member via a passage extending through at least a portion of a dimension of a third separation member.

22. The method of claim 21, wherein said check valve further selectively unseals the checked passage during at least one of said centrifuging the separation system in said container to allow at least a portion of the whole material to pass through said checked passage or during a said withdrawal of said fraction from said container to equalize a pressure during withdrawal of said fraction.

* * * * *